US010820790B2

(12) United States Patent
Nagae

(10) Patent No.: US 10,820,790 B2
(45) Date of Patent: Nov. 3, 2020

(54) IMAGE PICKUP DEVICE, MICROSCOPE IMAGE PICKUP SYSTEM, AND ENDOSCOPE IMAGE PICKUP SYSTEM

(71) Applicant: SONY CORPORATION, Tokyo (JP)

(72) Inventor: Satoshi Nagae, Tokyo (JP)

(73) Assignee: SONY CORPORATION, Tokyo (JP)

( * ) Notice: Subject to any disclaimer, the term of this patent is extended or adjusted under 35 U.S.C. 154(b) by 498 days.

(21) Appl. No.: 15/572,913

(22) PCT Filed: Jul. 1, 2016

(86) PCT No.: PCT/JP2016/003158
§ 371 (c)(1),
(2) Date: Nov. 9, 2017

(87) PCT Pub. No.: WO2017/043000
PCT Pub. Date: Mar. 16, 2017

(65) Prior Publication Data
US 2018/0132706 A1 May 17, 2018

(30) Foreign Application Priority Data
Sep. 7, 2015 (JP) ................................ 2015-175569

(51) Int. Cl.
*A61B 1/04* (2006.01)
*G01N 21/64* (2006.01)
(Continued)

(52) U.S. Cl.
CPC ............ *A61B 1/043* (2013.01); *A61B 1/0005* (2013.01); *A61B 1/00006* (2013.01);
(Continued)

(58) Field of Classification Search
CPC ............ G02B 210/0076; G02B 21/361; G02B 21/365; G02B 21/16; G02B 21/18;
(Continued)

(56) References Cited

U.S. PATENT DOCUMENTS 5,040,872 A  8/1991 Steinle
2002/0035330 A1  3/2002 Cline et al.
(Continued)

FOREIGN PATENT DOCUMENTS

CN  101385358 A  3/2009
CN  104274156 A  1/2015
(Continued)

OTHER PUBLICATIONS

Office Action issued in Japanese Application 2015-175569 dated May 28, 2019.
(Continued)

*Primary Examiner* — Bo Joseph Peng
(74) *Attorney, Agent, or Firm* — Xsensus LLP

(57) ABSTRACT

Provided is a medical imaging device comprising: a color separation prism that has a dichroic film configured to split light into first light belonging to a visible light wavelength band and second light belonging to a fluorescence wavelength band; a fluorescence image sensor that is provided at an output side of the color separation prism and that is configured to image at least part of the second light belonging to the fluorescence wavelength band separated by the dichroic film; a visible light image sensor that is provided at the output side of the color separation prism and that is configured to image at least part of the first light belonging to the visible light wavelength band separated by the dichroic film; and a bandpass filter that is disposed between the color separation prism and the fluorescence image sensor, wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light
(Continued)

imaged on the visible light image sensor via the color separation prism corresponds to an amount of a shift between a fluorescence imaging position and a visible light imaging position, the shift being generated by an imaging lens positioned at an input side of the color separation prism, and wherein the fluorescence imaging position is an imaging position of filtered second light, which results from passing the second light through the bandpass tiller, such that tlic amoiuu of shifl is based on the filtered second light.

20 Claims, 10 Drawing Sheets

(51) Int. Cl.
    *G02B 21/16*   (2006.01)
    *G02B 27/10*   (2006.01)
    *G02B 21/36*   (2006.01)
    *G02B 21/00*   (2006.01)
    *A61B 1/00*    (2006.01)
    *A61B 5/00*    (2006.01)
    *A61B 1/055*   (2006.01)
    *G02B 21/18*   (2006.01)

(52) U.S. Cl.
    CPC ...... *A61B 1/00186* (2013.01); *A61B 1/00188* (2013.01); *A61B 1/042* (2013.01); *A61B 1/055* (2013.01); *A61B 5/0071* (2013.01); *G01N 21/6458* (2013.01); *G02B 21/0076* (2013.01); *G02B 21/16* (2013.01); *G02B 21/18* (2013.01); *G02B 21/361* (2013.01); *G02B 21/365* (2013.01); *G02B 27/1013* (2013.01); *A61B 2562/0242* (2013.01); *G01N 21/6456* (2013.01); *G01N 2021/6463* (2013.01)

(58) Field of Classification Search
    CPC . G02B 27/1013; A61B 1/055; A61B 1/00006; A61B 1/0005; A61B 1/043; A61B 1/00188; A61B 1/042; A61B 1/00186; A61B 5/0071; A61B 2562/0242; G01N 21/6458; G01N 21/6456; G01N 2021/6463

See application file for complete search history.

(56) References Cited

U.S. PATENT DOCUMENTS

| | | |
|---|---|---|
| 2005/0065406 A1 | 3/2005 | Cline et al. |
| 2008/0228037 A1 | 9/2008 | Cline et al. |
| 2010/0079587 A1 | 4/2010 | Yoshida |
| 2010/0145416 A1 | 6/2010 | Kang et al. |
| 2010/0198010 A1 | 8/2010 | Cline et al. |
| 2010/0210904 A1 | 8/2010 | Cline et al. |
| 2011/0001061 A1 | 1/2011 | Ishihara |
| 2013/0041216 A1 | 2/2013 | McDowall |
| 2014/0225992 A1 | 8/2014 | McDowall |
| 2015/0230698 A1 | 8/2015 | Cline et al. |

FOREIGN PATENT DOCUMENTS

| | | |
|---|---|---|
| JP | 02-077001 A | 3/1990 |
| JP | 08-032979 A | 2/1996 |
| JP | 10-133126 A | 5/1998 |
| JP | 10-201707 A | 8/1998 |
| JP | 10-325798 A | 12/1998 |
| JP | 2001-147381 A | 5/2001 |
| JP | 2013-3495 A | 1/2013 |
| JP | 2015-16332 A | 1/2015 |

OTHER PUBLICATIONS

International Search Report dated Oct. 27, 2016 in PCT/JP2016/003158, filed on Jul. 1, 2016.
Chinese Office Action dated Sep. 3, 2019, issued in corresponding Chinese Patent Application No. 2016800499549.

[Fig. 1A]
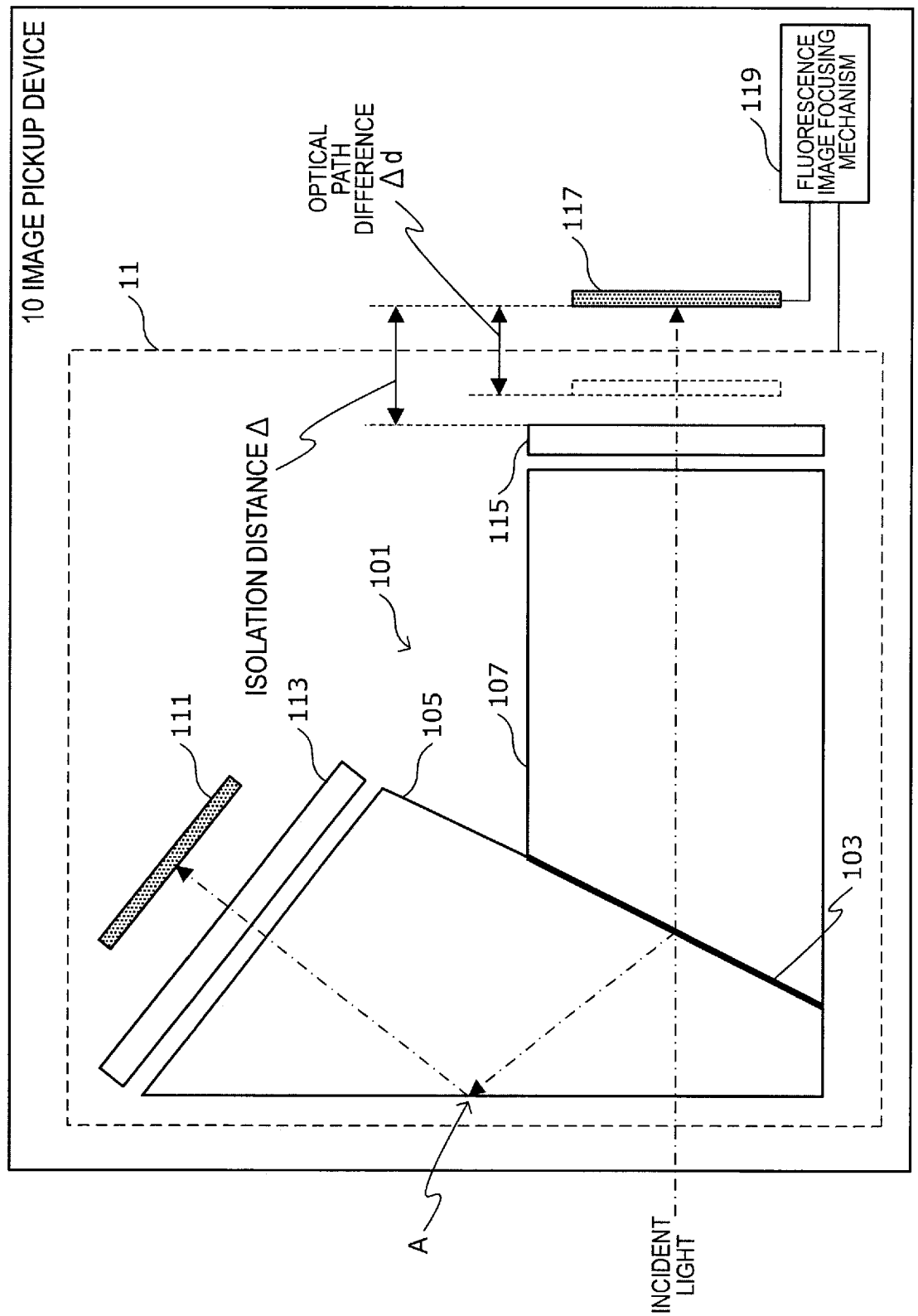

[Fig. 1B]
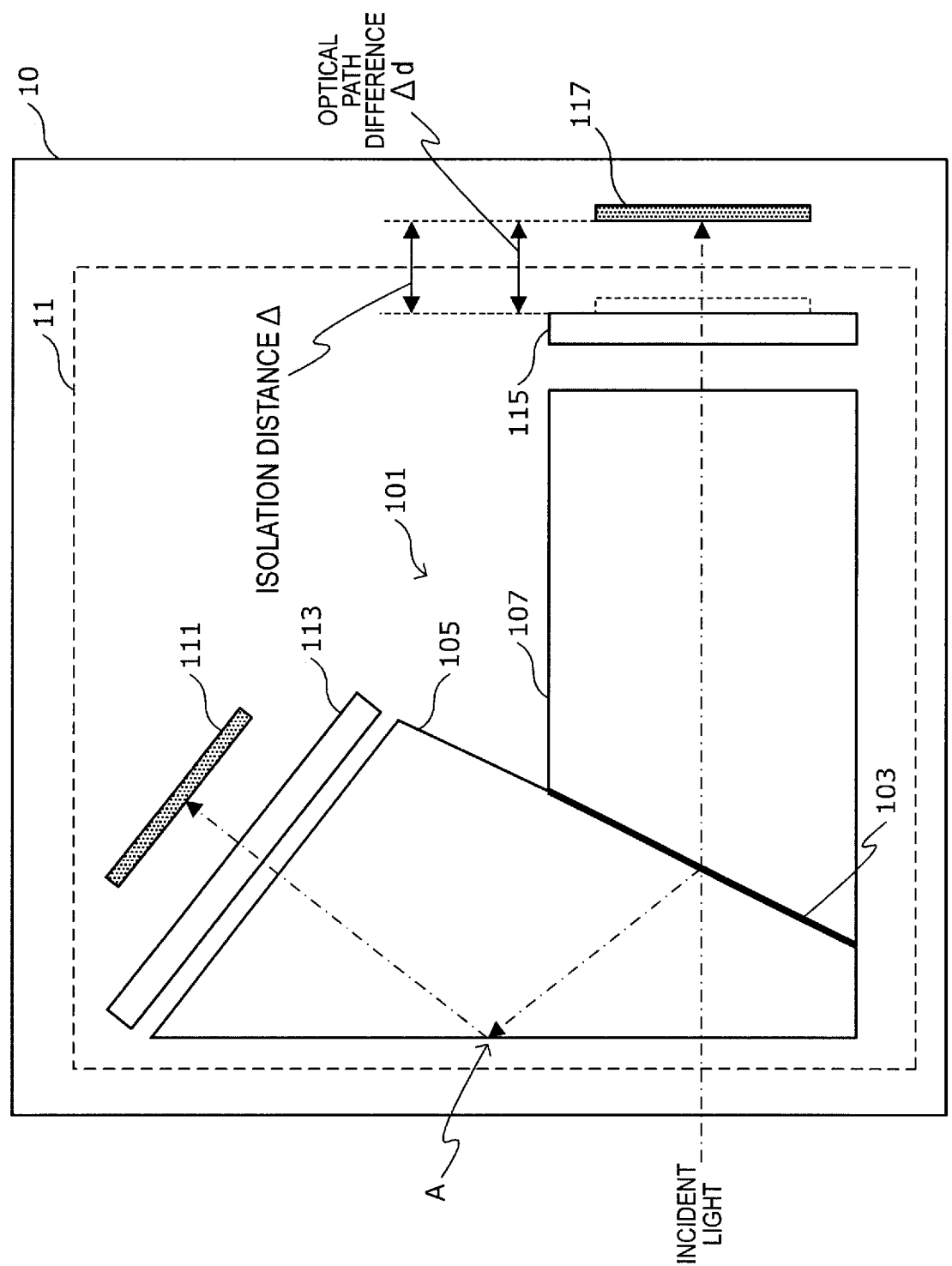

[Fig. 2]
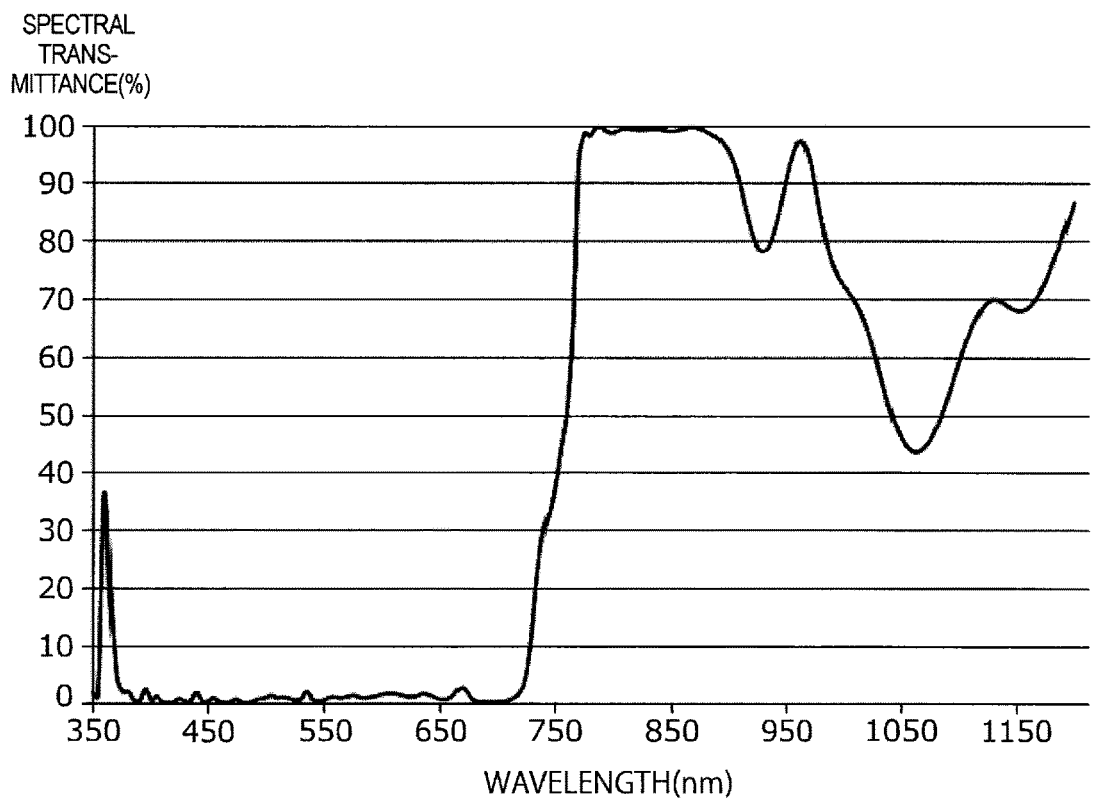
[Fig. 3]
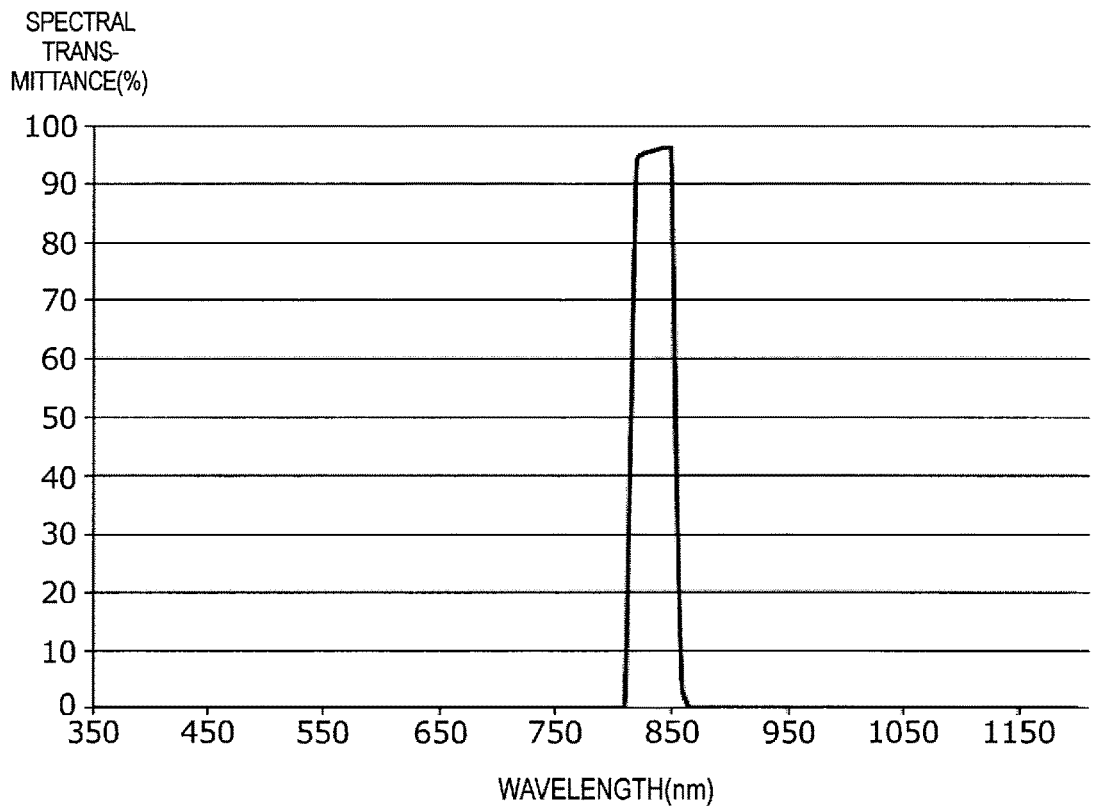

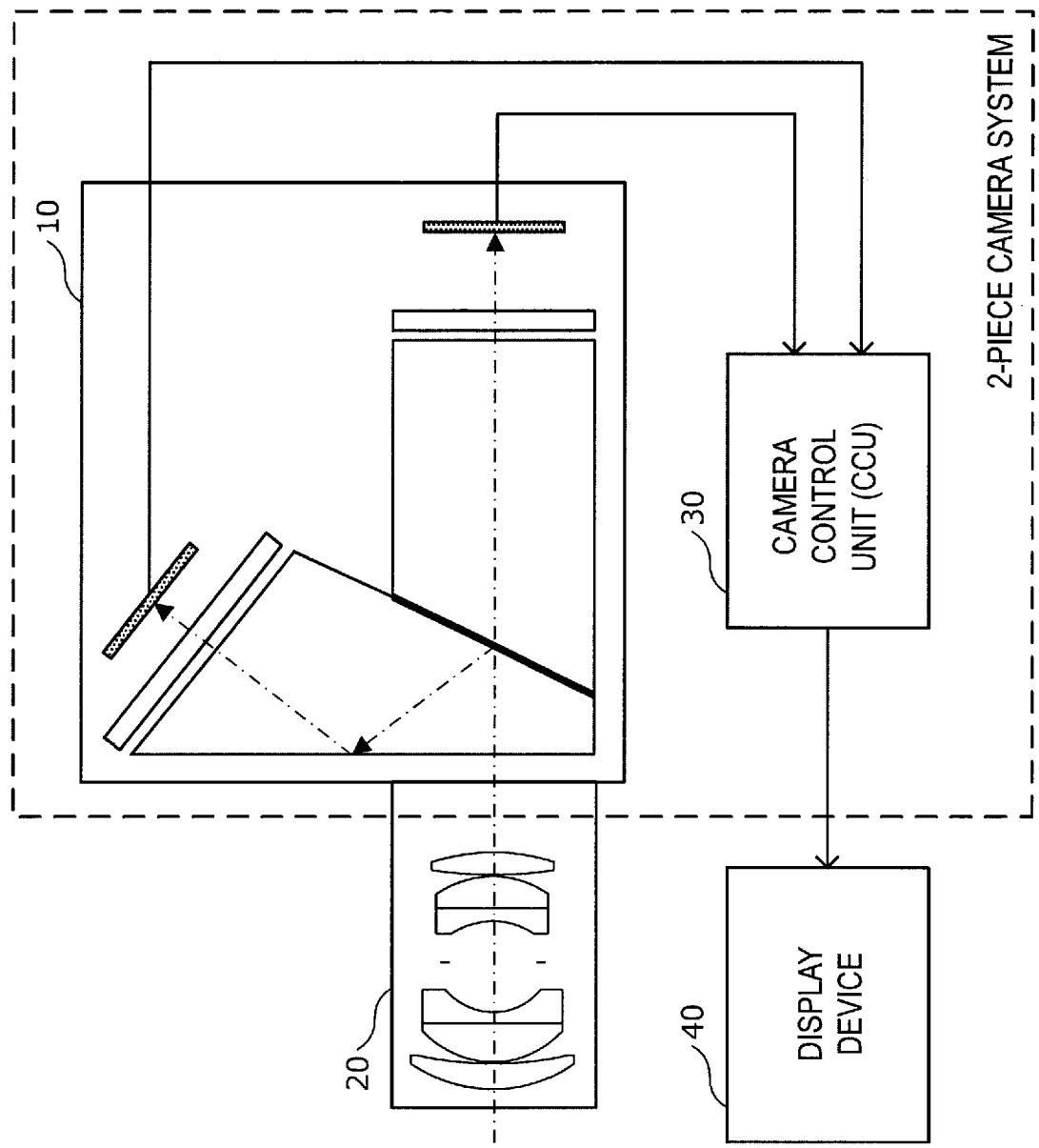
[Fig. 4]

[Fig. 5]
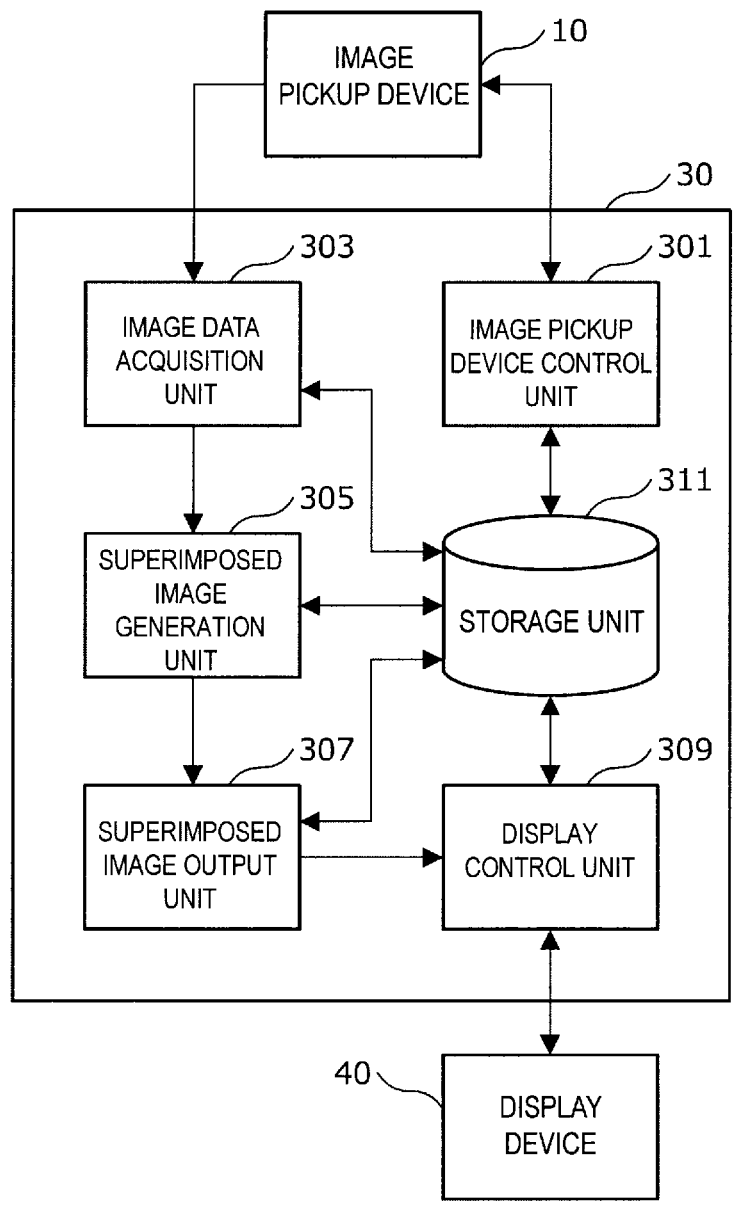

[Fig. 6]
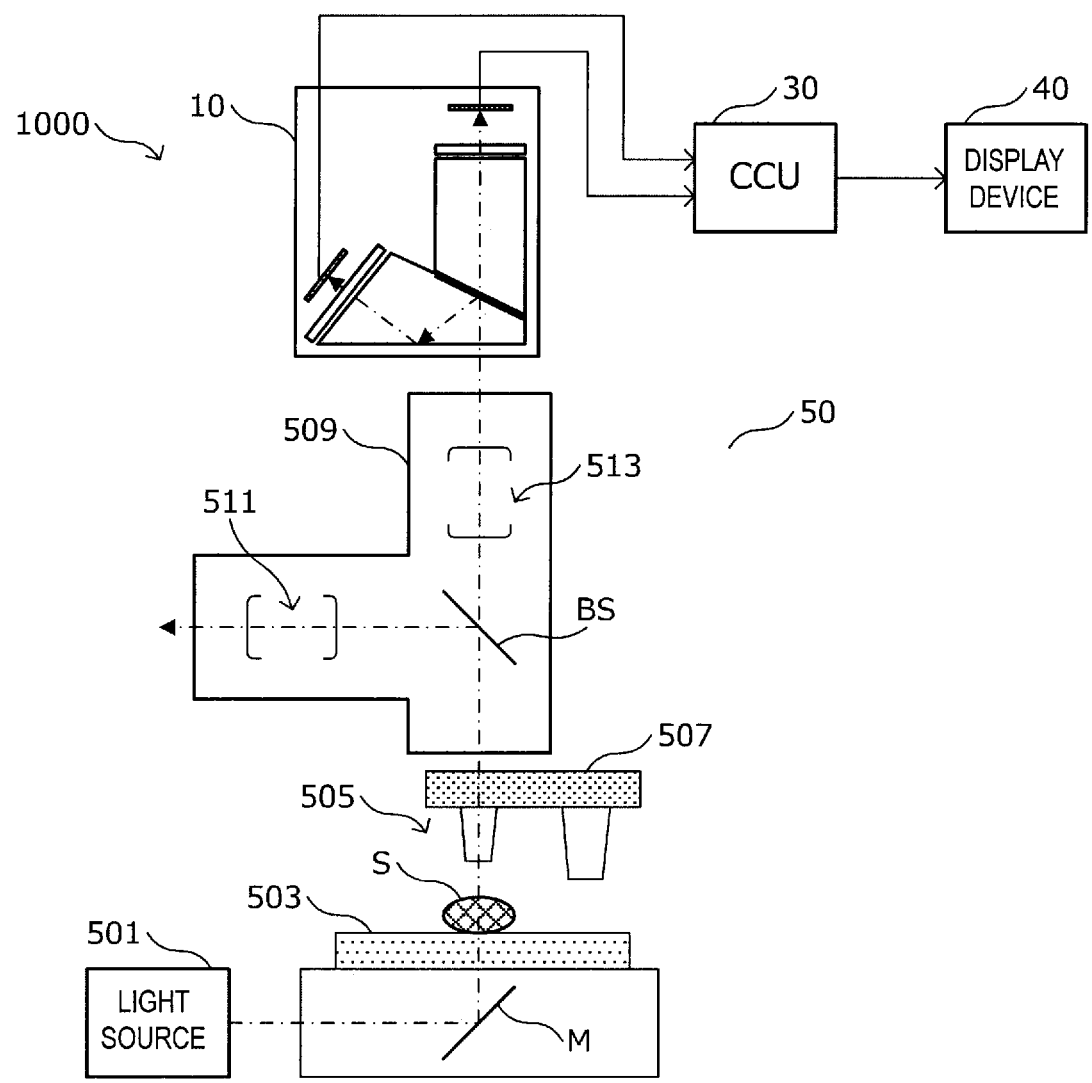

[Fig. 7A]
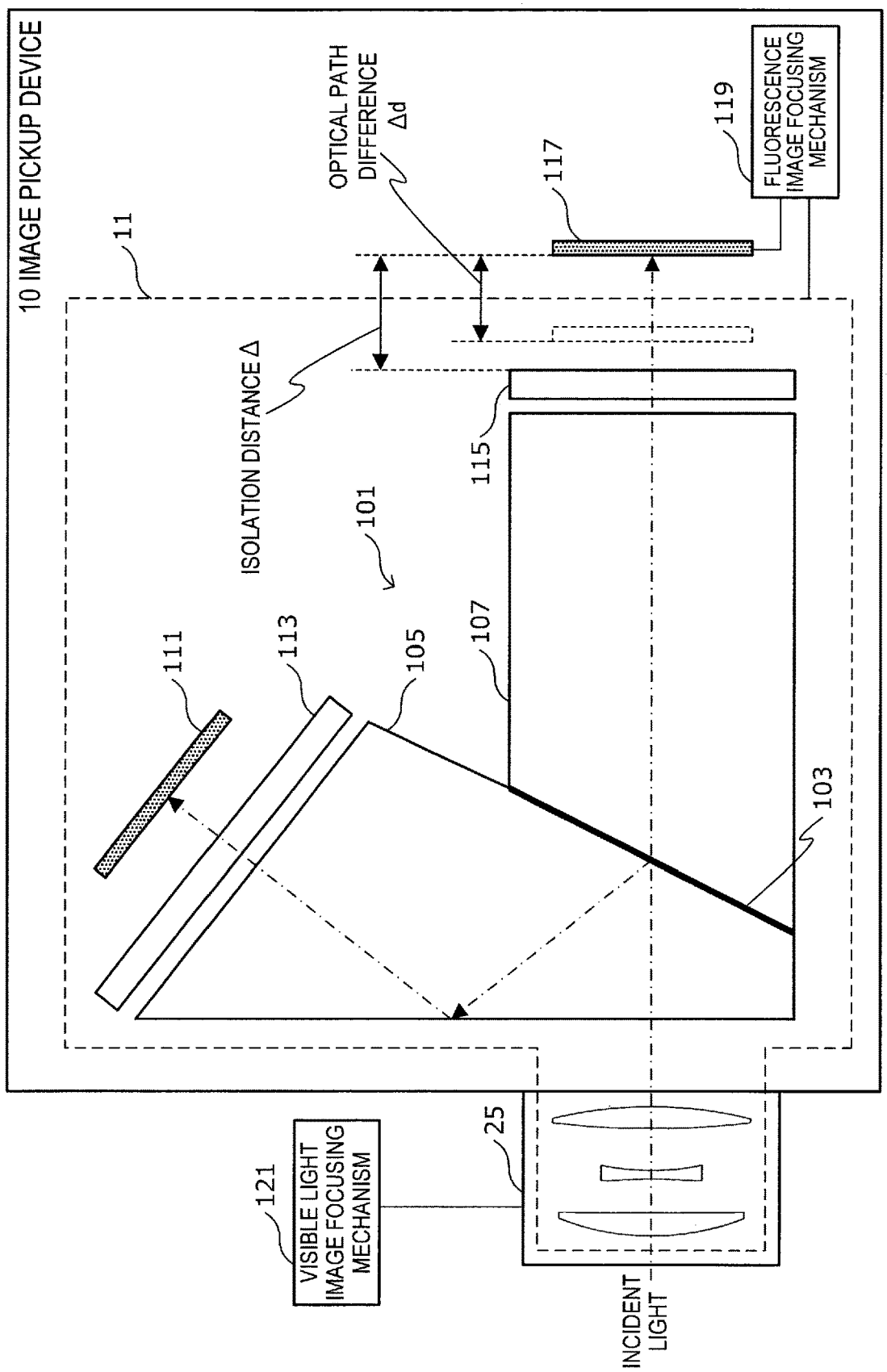

[Fig. 7B]
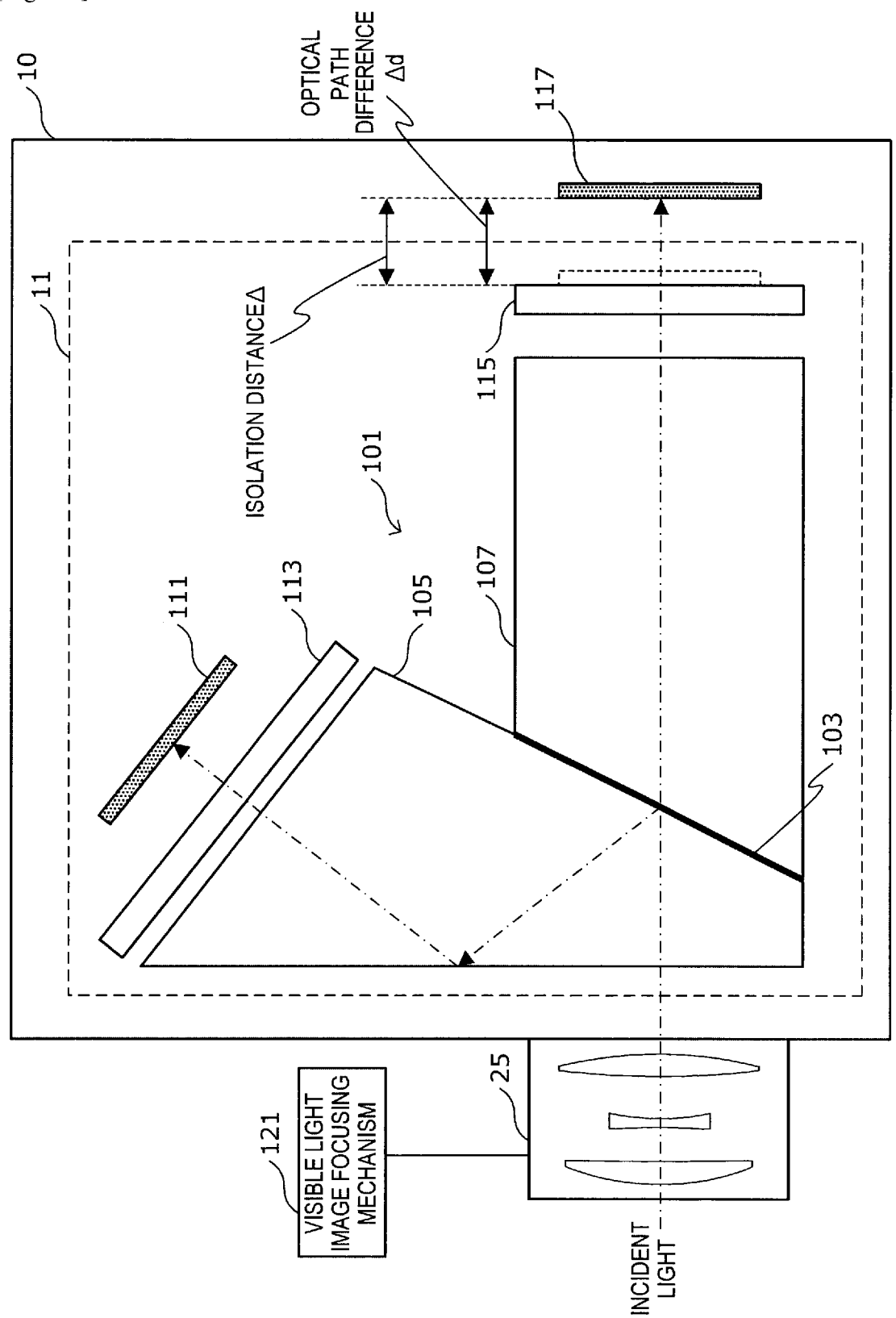

[Fig. 8]
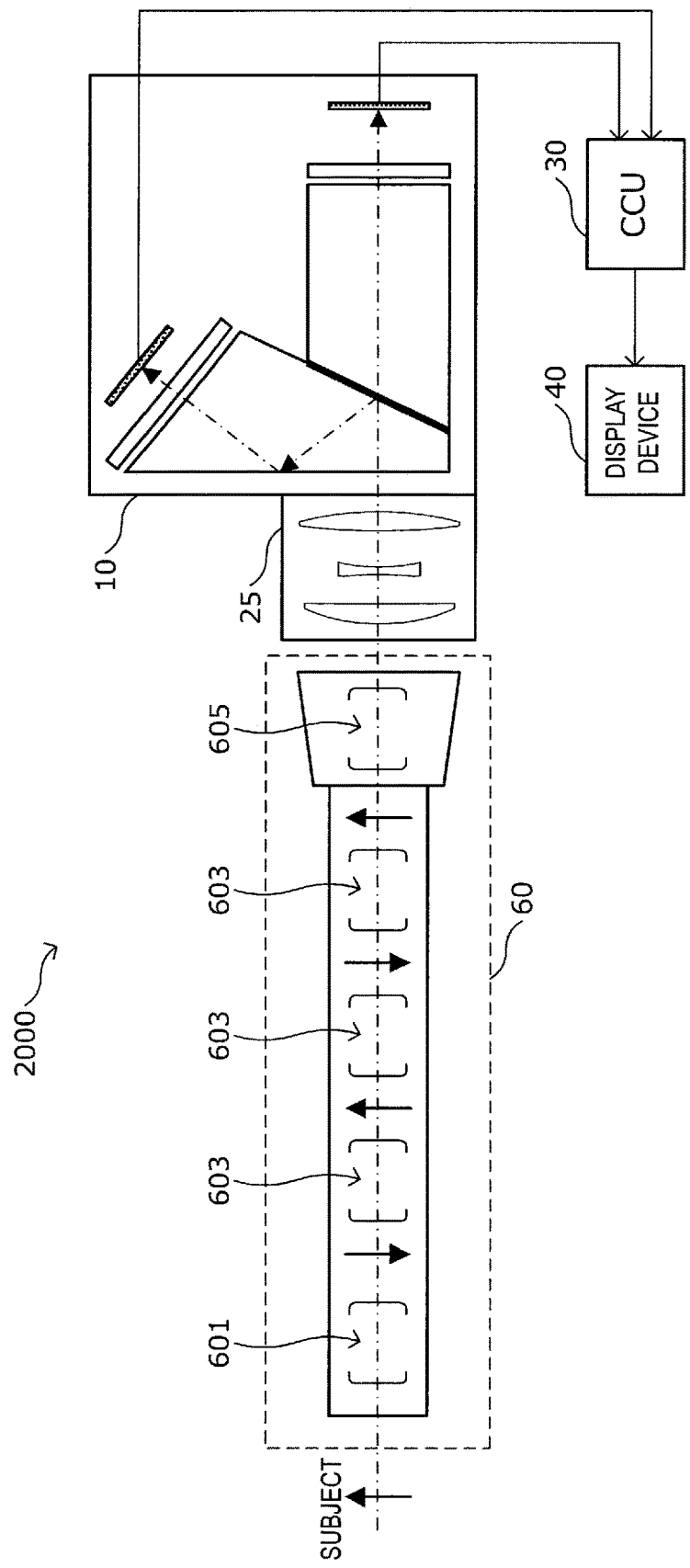

[Fig. 9]
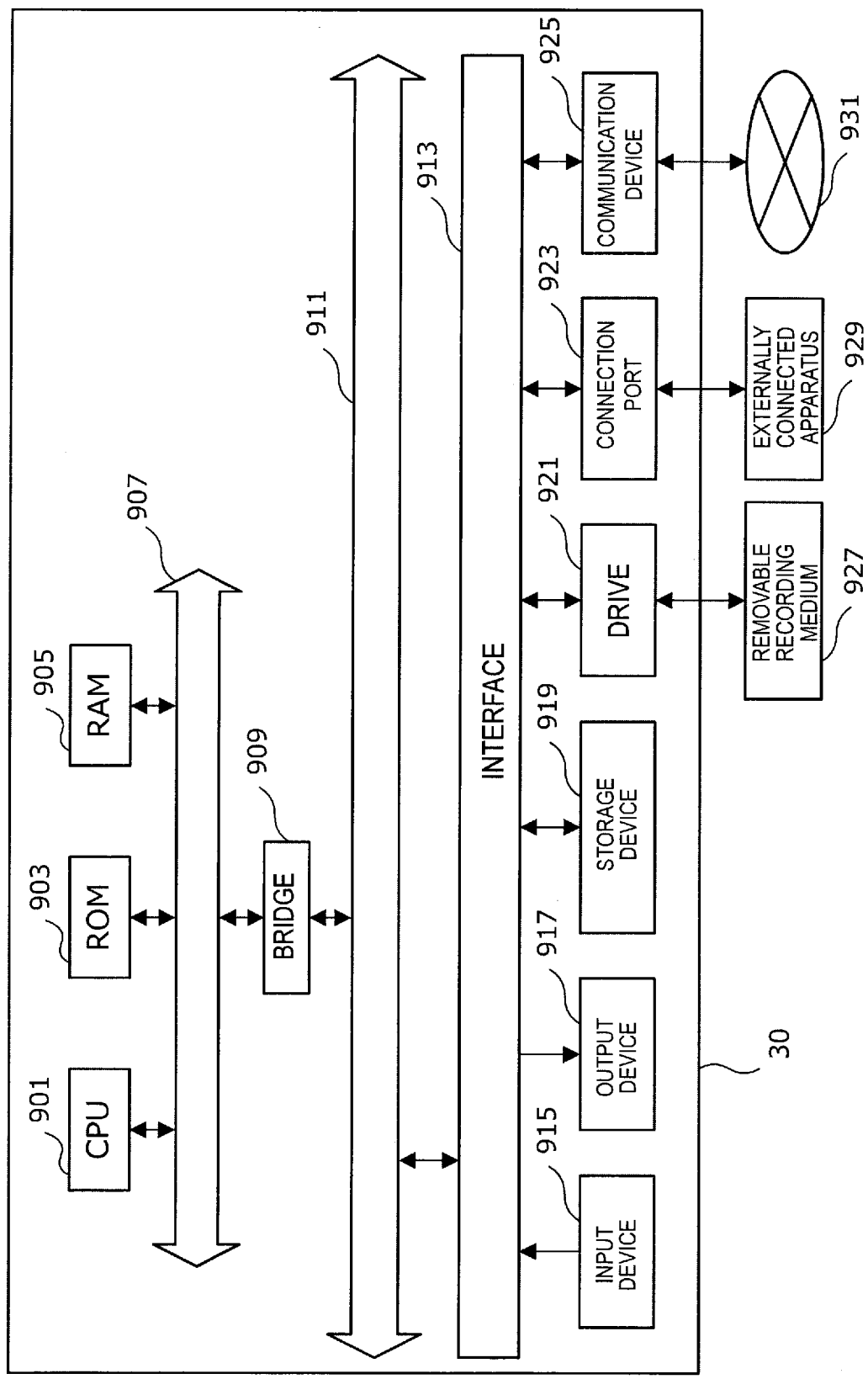

IMAGE PICKUP DEVICE, MICROSCOPE IMAGE PICKUP SYSTEM, AND ENDOSCOPE IMAGE PICKUP SYSTEM

CROSS REFERENCE TO RELATED APPLICATIONS

This application claims the benefit of Japanese Priority Patent Application JP 2015-175569 filed Sep. 7, 2015, the entire contents of which are incorporated herein by reference.

TECHNICAL FIELD

The present disclosure relates to an image pickup device, a microscope image pickup system, and an endoscope image pickup system.

BACKGROUND ART

There is known a technology (photodynamic diagnosis/treatment technology) for ad-ministering any of various fluorescent probes to a patient, emitting excitation light for exciting the fluorescent probe when the fluorescent probe is accumulated on a cancer tissue or the like, observing near-infrared fluorescence having a predetermined wavelength emitted from the fluorescent probe to specify a position of an affected part (that is, the cancer tissue) to thereby perform diagnosis and treatment. A wavelength of the excitation light for exciting the fluorescent probe and a wavelength of the near-infrared fluorescence emitted from the fluorescent probe are inherent to a fluorescent probe to be used, and, in the case where, for example, indocyanine green is used as a fluorescent probe, light having a wavelength of about 769 nm is used as excitation light, and fluorescence having a wavelength of about 832 nm is emitted from indocyanine green.

In the above photodynamic diagnosis/treatment technology, fluorescence is observed in a dark state in which indoor lighting is off because obtainable fluorescence intensity is weak. Thus, a doctor recognizes an image in which a fluorescence part is luminous in a dark field of vision, and therefore it is difficult to specify a position of the fluorescence part in the whole affected part. As a result, the doctor recognizes the affected part while switching observation with visible light and observation with fluorescence and then implements diagnosis or treatment. Thus, processing is complicated. In order to solve such a circumstance, various matters of an image pickup system for performing superimposed display of a fluorescence image and a visible light image in real time have been studied.

For example, PTL 1 cited below discloses a microscope system including: branch optical mechanism for dividing, into two parts, an observed luminous flux extracted to the outside from an affected part to which a fluorescent probe has been administered; fluorescence image pickup mechanism connected to one end of the branch optical mechanism; and visible light image pickup mechanism connected to the other end of the branch optical mechanism; and display mechanism for displaying a fluorescence image captured by the fluorescence image pickup mechanism and a visible light image captured by the visible light image pickup mechanism so that the fluorescence image and the visible light image are superimposed, in which the branch optical mechanism is an optical block having an interface for coaxially separating only fluorescence having a predetermined wavelength from visible light in the observed luminous flux.

PTL 2 described below discloses a near-infrared fluorescence detection device for detecting near-infrared fluorescence from a fluorescent material accumulated on a sentinel lymph node inside a body. More specifically, the near-infrared fluorescence detection device splits reflected light and near-infrared fluorescence from an observation target into visible-light reflected light and near-infrared fluorescence by using a beam splitter such as a dichroic prism, then detects the visible reflection light and the near-infrared fluorescence to thereby form a visible reflection light image signal and a near-infrared fluorescence signal, and outputs a composite image obtained by combining the visible-light video signal and the near-infrared fluorescence signal. Herein, PTL 2 cited below discloses that visible reflection light is detected by a color image sensor, whereas near-infrared fluorescence is detected by a monochrome image sensor, and the monochrome image sensor is disposed to be isolated from the beam splitter at a predetermined distance (A), as compared with the color image sensor, in order to correct axial chromatic aberration.

CITATION LIST

Patent Literature

PTL 1: JP 2013-3495A
PTL 2: JP 2015-16332A

SUMMARY

Technical Problem

However, in PTL 1 cited above, because only a fluorescence component is attempted to be extracted from an incident observed luminous flux by using only an optical multilayer film having a characteristic that "the branch optical mechanism is an optical block having an interface for coaxially separating only fluorescence having a predetermined wavelength from visible light in the observed luminous flux", costs for manufacturing the optical multilayer film are increased and a desired spectral characteristic is not achieved.

PTL 2 cited above neither discloses a condition that is necessary for a spectral characteristic of the beam splitter for splitting near-infrared fluorescence nor a method of achieving an isolation distance Δ. Therefore, depending on a spectral characteristic of fluorescence from the observation target, axial chromatic aberration is not completely corrected and a favorable superimposed image is not obtained.

As described above, in the technologies disclosed in PTL 1 and PTL 2 cited above, light from an observation target is not split into a visible light component and a fluorescence component with high accuracy, and a favorable superimposed image obtained by superimposing a visible light image and a fluorescence image is not obtained.

In view of the above circumstances, embodiments of the present disclosure propose an image pickup device, a microscope image pickup system, and an endoscope image pickup system, each of which is capable of splitting light from an observation target into a visible light component and a fluorescence component with high accuracy and is capable of obtaining a favorable superimposed image by superimposing a visible light image and a fluorescence image on each other.

Solution to Problem

According to an embodiment of the present disclosure, there is provided medical imaging device including a color separation prism that has a dichroic film configured to split light into first light belonging to a visible light wavelength band and second light belonging to a fluorescence wavelength band, a fluorescence image sensor that is provided at an output side of the color separation prism and that is configured to image at least part of the second light belonging to the fluorescence wavelength band separated by the dichroic film, a visible light image sensor that is provided at the output side of the color separation prism and that is configured to image at least part of the first light belonging to the visible light wavelength band separated by the dichroic film, and a bandpass filter that is disposed between the color separation prism and the fluorescence image sensor. The fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism. The fluorescence imaging position is an imaging position of filtered second light, which results from passing the second light through the bandpass filter, such that the amount of shift is based on the filtered second light.

According to an embodiment of the present disclosure, there is provided a medical microscopic system including a microscopic optical lens assembly including at least an objective lens and an imaging lens, and an imaging device configured to capture a magnified image of an object. The imaging device includes a color separation prism that has a dichroic film configured to split light into first light belonging to the visible light wavelength band and second light belonging to the fluorescence wavelength band, a fluorescence image sensor that is provided at an output side of the color separation prism and that is configured to image at least part of the second light belonging to the fluorescence wavelength band separated by the dichroic film, a visible light image sensor that is provided at the output side of the color separation prism and that is configured to image at least part of the first light belonging to the visible light wavelength band separated by the dichroic film, and a bandpass filter that is disposed between the color separation prism and the fluorescence image sensor. The fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism. The fluorescence imaging position is an imaging position of filtered second light, which results from passing the second light through the bandpass filter, such that the amount of shift is based on the filtered second light.

According to an embodiment of the present disclosure, there is provided an endoscopic system including an endoscopic optical lens assembly, an imaging device configured to capture an image of an object, and an coupler optical lens assembly that is provided between the endoscopic optical lens assembly and the imaging device. The imaging device includes a color separation prism that has a dichroic film configured to split light into first light belonging to the visible light wavelength band and second light belonging to the fluorescence wavelength band, a fluorescence image sensor that is provided at an output side of the color separation prism and that is configured to image at least part of the second light belonging to the fluorescence wavelength band separated by the dichroic film, a visible light image sensor that is provided at the output side of the color separation prism and that is configured to image at least part of the first light belonging to the visible light wavelength band separated by the dichroic film, and a bandpass filter that is disposed between the color separation prism and the fluorescence image sensor. The fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism. The fluorescence imaging position is an imaging position of filtered second light, which results from passing the second light through the bandpass filter, such that the amount of shift is based on the filtered second light.

Accordingly in the present embodiments, axial chromatic aberration contained in fluorescence imaged by the fluorescence image sensor is completely corrected by setting arrangement positions of the fluorescence image sensor and the visible light image sensor as described above.

Advantageous Effects of Invention

As described above, according to an embodiment of the present disclosure, it is possible to split light from an observation target into a visible light component and a fluorescence component with high accuracy and to obtain a favorable superimposed image by superimposing a visible light image and a fluorescence image on each other.

Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1A is an explanatory diagram schematically illustrating an example of a configuration of an image pickup device according to an embodiment of the present disclosure.

FIG. 1B is an explanatory diagram schematically illustrating an example of the configuration of the image pickup device according to the embodiment.

FIG. 2 is a graph showing an example of a spectral transmittance characteristic of a dichroic film provided in the image pickup device according to the embodiment.

FIG. 3 is a graph showing an example of a spectral transmittance characteristic of a bandpass filter provided in the image pickup device according to the embodiment.

FIG. 4 is an explanatory diagram schematically illustrating an example of a configuration of a 2-piece camera system including the image pickup device according to the embodiment.

FIG. 5 is a block diagram showing an example of a configuration of a camera control unit that can be used for the image pickup device according to the embodiment.

FIG. 6 is an explanatory diagram schematically illustrating an example of a configuration of a microscope image pickup system including the image pickup device according to the embodiment.

FIG. 7A is an explanatory diagram schematically illustrating another example of the configuration of the image pickup device according to the embodiment.

FIG. 7B is an explanatory diagram schematically illustrating another example of the configuration of the image pickup device according to the embodiment.

FIG. 8 is an explanatory diagram schematically illustrating an example of a configuration of an endoscope image pickup system including the image pickup device according to the embodiment.

FIG. 9 is a block diagram showing an example of a hardware configuration of the camera control unit that can be used for the image pickup device according to the embodiment.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that the following description is given in the order indicated below.
1. Study by Inventor of the Present Disclosure
2. First Embodiment
2.1 Example of Configuration of Image Pickup Device
2.2 2-piece Camera System Including Image Pickup Device
2.3 Configuration of Camera Control Unit That Can Be Used for Image Pickup Device
2.4 Microscope Image Pickup System Including Image Pickup Device
2.5 Another Example of Configuration of Image Pickup Device
2.6 Endoscope Image Pickup System Including Image Pickup Device
3. Hardware Configuration of Camera Control Unit (Study by Inventor of the Present Disclosure)

Prior to description of an image pickup device, a microscope image pickup system, and an endoscope image pickup system according to an embodiment of the present disclosure, the content of study performed by the inventor of the present disclosure regarding an image pickup system for performing superimposed display of a fluorescence image and a visible light image in real time will be briefly described, and what the embodiment of the present disclosure aims at will be briefly described.

Prior to study of the image pickup device according to the embodiment of the present disclosure, the inventor of the present disclosure first studied a technology disclosed in PTL 1 cited above. As a result, the inventor found that it was important to further study the technology disclosed in PTL 1 cited above regarding the following points. That is, in PTL 1 cited above, only a fluorescence component is attempted to be extracted from an incident observed luminous flux by using only an optical multilayer film having a characteristic that "the branch optical mechanism is an optical block having an interface for coaxially separating only fluorescence having a predetermined wavelength from visible light in the observed luminous flux". However, the inventor of the present disclosure found that there were problems described below in order to extract only the fluorescence component.

First, in PTL 1 cited above, the above optical block functioning as the branch optical mechanism is attempted to be achieved by adhering two prisms to each other and providing the optical multilayer film having the above characteristic between adhered surfaces. At this time, in order to split an optical path into an optical path of visible light and an optical path of near-infrared fluorescence, the adhered surfaces of the prisms (in other words, an interface between the two prisms) of the optical block are inclined with respect to an optical axis, and an angle of incidence of beams of light to the interface is increased.

Herein, it is known that the characteristic of the optical multilayer film is changed in accordance with an angle of incidence of beams of light to be incident thereon. That is, a spectral characteristic of the optical multilayer film is originally designed assuming that beams of light are vertically incident on the multilayer film. However, as described in PTL 1 cited above, in the case where an angle of incidence of beams of light is increased, and, as a result, the beams of the light are not vertically incident on the optical multilayer film, it is important to increase the number of optical thin films included in the optical multilayer film in order to achieve the same spectral characteristic as a spectral characteristic obtained when beams of light are vertically incident thereon. As a result, it is difficult to reduce a size of an optical prism and costs are increased. In the case where beams of light having a bright f-number are incident on the optical prism disclosed in PTL 1 cited above, a change in spectral characteristic caused by a difference in angle of incidence between upper beams of light and lower beams of light is not suppressed. Thus, a desired spectral characteristic is not achieved.

That is, in the technology disclosed in PTL 1 cited above, the following matter for study exists: the characteristic of the optical multilayer film for dividing beams of light into two parts, the number of arranged optical multilayer films, and a positional rela-tionship with the optical multilayer film are not preferable.

It can also be considered that axial chromatic aberration is greatly generated in a fluorescence wavelength band depending on a spectral characteristic of a fluorescence image to be focused on. Regarding this point, the technology disclosed in PTL 2 cited above attempts to correct axial chromatic aberration by disposing the monochrome image sensor so that the monochrome image sensor is isolated from the beam splitter at a distance Δ, as compared with the color image sensor. However, as a result of study performed by the inventor of the present disclosure, it is found that, even in the case where a difference in the center of chromatic aberration between a visible light wavelength band and the fluorescence wavelength band is corrected by providing the isolation distance Δ, components of wavelengths other than a central wavelength in the fluorescence wavelength band form a blur image and a contrast is reduced. That is, it is found that the effect of the isolation distance Δ is not satisfactorily exerted in some cases in the technology disclosed in PTL 2 cited above. Because PTL 2 cited above neither discloses a condition that is necessary for a spectral characteristic of an optical filter nor a method of achieving the isolation distance Δ, PTL 2 cited above discloses no method of completely correcting axial chromatic aberration.

Therefore, the method of completely correcting axial chromatic aberration is a matter for study.

The inventor of the present disclosure found the above matters for study and then focused on an image pickup system capable of performing superimposed display of a visible light image and a fluorescence image in real time. Such an image pickup system can be achieved by using an image pickup device capable of separating a visible light image and a fluorescence image with high accuracy and a control unit that controls the image pickup device.

An example of the image pickup system is a medical CMOS full HD video camera including a camera head unit (CHU) and a camera control unit (CCU) (Hereinafter, such an image pickup system including a CHU and a CCU will be also referred to as "2-piece camera".). In the image pickup system, the CHU includes a single-plate image pickup element having an RGB color filter or a 3-color separation prism module, and a user can capture a full-HD image with high color reproducibility by attaching an arbitrary imaging lens (various kinds of optical systems such as a microscope and an endoscope) to the CHU.

An example of the similar image pickup system is a CHU for a rigid endoscope. The CHU for a rigid endoscope includes a coupler optical system, and an eyepiece unit of the rigid endoscope is detachable from the CHU. In the CHU, the coupler optical system images a substantially afocal luminous flux from the eyepiece unit on an image pickup element.

In the above image pickup system, depending on an optical system (imaging lens or rigid endoscope) to be used by a user, axial chromatic aberration is generated between the visible light wavelength band and the fluorescence wavelength band, and imaging positions thereof are different in an optical axis direction. As a result, when a visible light image is focused in the CHU, a fluorescence image is not focused, whereas, when the fluorescence image is focused, the visible light image is not focused. That is, both the images are not simultaneously captured with the best pint. Therefore, in related arts, observation is performed on an average image surface while a balance is being kept between visible light and fluorescence. In particular, even in the case where the optical system to be used by the user has an MTF of full-HD resolution, the CHU does not satisfactorily exert resolution performance when the CHU has the matters for study in the technologies disclosed in PTL 1 and PTL 2 cited above.

In view of this, the inventor of the present disclosure has diligently studied to solve the above matters for study and achieve an image pickup device (CHU) capable of splitting light into visible light and fluorescence with high accuracy even in the case where a user uses an arbitrary optical system. As a result, the inventor has arrived at a method of solving the above matters for study and have arrived at an image pickup device capable of splitting light into visible light and fluorescence with high accuracy. When the image pickup device is used, it is possible to superimpose visible light and fluorescence in a state in which both the visible light and the fluorescence are focused. Therefore, it is possible to achieve an image pickup system capable of generating a better superimposed image.

Hereinafter, the image pickup device that has been completed as a result of diligent study by the inventor of the present disclosure and a microscope image pickup system and an endoscope image pickup system each of which includes the image pickup device will be described in detail.

First Embodiment

Hereinafter, an image pickup device, a microscope image pickup system, and an endoscope image pickup system according to a first embodiment of the present disclosure will be described in detail with reference to the drawings.

Note that, hereinafter, there will be described an example where fluorescence having a wavelength of 832 nm belonging to a near-infrared band, the fluorescence being emitted from indocyanine green (excitation wavelength: about 769 nm), is focused on. However, even in the case where fluorescence belonging to another wavelength band is focused on, it is possible to similarly apply a technical idea of an embodiment of the present disclosure by changing spectral characteristics of a dichroic film and a bandpass filter described below to spectral characteristics thereof suitable for fluorescence to be focused on.

<Example of Configuration of Image Pickup Device>

An example of a configuration of an image pickup device according to the embodiment will be described in detail with reference to FIG. 1A to FIG. 3. FIG. 1A and FIG. 1B are explanatory diagrams each of which schematically illustrates an example of the configuration of the image pickup device according to the embodiment. FIG. 2 is a graph showing an example of a spectral transmittance characteristic of a dichroic film provided in the image pickup device according to the embodiment. FIG. 3 is a graph showing an example of a spectral transmittance characteristic of a bandpass filter provided in the image pickup device according to the embodiment.

In the case where incident light containing both light belonging to the visible light wavelength band and light belonging to the fluorescence wavelength band is incident on the image pickup device according to the embodiment, the image pickup device splits the incident light into the light belonging to the visible light wavelength band and the light belonging to the fluorescence wavelength band with high accuracy and then independently captures images of the light belonging to the respective wavelength bands to generate a visible light captured image (hereinafter, also simply referred to as "visible light image") and a fluorescence captured image (hereinafter, also simply referred to as "fluorescence image").

As schematically illustrated in, for example, FIG. 1A, such an image pickup device 10 includes at least a color separation prism 101, a visible light image pickup element 111, a bandpass filter 115, and a fluorescence image pickup element 117.

The color separation prism 101 is an optical member that splits incident light incident on the image pickup device 10 into light belonging to the visible light wavelength band and light belonging to the fluorescence wavelength band. The color separation prism 101 includes a dichroic film 103 for splitting light into light belonging to the visible light wavelength band and light belonging to the fluorescence wavelength band.

The dichroic film 103 is an optical film that splits incident light incident on the color separation prism 101, the incident light containing light belonging to the visible light wavelength band and light belonging to the fluorescence wavelength band, into the light belonging to the visible light wavelength band and the light belonging to the fluorescence wavelength band. FIG. 2 shows an example of a spectral transmittance characteristic of the dichroic film 103 according to the embodiment. In FIG. 2, a horizontal axis indicates a wavelength of light (unit: nm) incident on the dichroic film 103, whereas a vertical axis indicates spectral transmittance (unit: %).

In the case where fluorescence having a wavelength of 832 nm belonging to the near-infrared band, the fluorescence being emitted from indocyanine green, is focused on, as shown in FIG. 2, the spectral transmittance of the dichroic film 103 preferably has a characteristic that reflects light in the visible light wavelength band and allows light in a near-infrared wavelength band to transmit therethrough. More specifically, as shown in FIG. 2, the dichroic film 103 preferably has transmittance of 90% or more in a wavelength band from 780 nm to 880 nm and transmittance of 10% or less in a wavelength band from 400 nm to 720 nm.

The transmittance of less than 90% in the wavelength band from 780 nm to 880 nm is not preferable because a ratio of fluorescence that is not transmitted through the dichroic film 103 is increased and brightness of a fluorescence image is reduced. Such a case is also not preferable in terms of image quality of a visible light image because fluorescence leaks into the visible light image pickup element 111 to thereby reduce a contrast of the visible light image.

The transmittance exceeding 10% in the wavelength band from 400 nm to 720 nm is not preferable because a ratio of visible light that is not reflected by the dichroic film 103 but is transmitted therethrough is increased and brightness of a visible light image is reduced. Such a case is also not preferable in terms of image quality of a fluorescence image because visible light leaks into the fluorescence image pickup element 117 to thereby reduce a contrast of the fluorescence image.

As is clear from FIG. 2 and the above description, the dichroic film 103 according to the embodiment splits incident light into two colors, i.e., light belonging to a predetermined fluorescence wavelength band and a band of longer wavelengths than the predetermined fluorescence wavelength band and light belonging to a band of shorter wavelengths than the predetermined fluorescence wavelength band. More specifically, the dichroic film 103 having the characteristic shown in FIG. 2 is a film functioning like a low-pass filter that splits incident light into two groups by setting a boundary to 750 nm which is a boundary between the visible light wavelength band and the fluorescence wavelength band.

Accordingly, the spectral characteristic of the dichroic film 103 according to the embodiment is comparatively broad as shown in FIG. 2, and, in the case where the dichroic film 103 is achieved as an optical multilayer film, the number of layers of the film can be reduced to about several tens of layers and a general vacuum deposition method can be used as a manufacturing method thereof. In the optical multilayer film disclosed in PTL 1 cited above, it is necessary to have an extraordinarily large number of layers of the film to achieve a function of extracting only fluorescence that is focused on by using only the optical multilayer film. Instead of extracting only fluorescence that is focused on by using only the dichroic film 103, the dichroic film 103 according to the embodiment only separates light in a long-wavelength band containing fluorescence that is focused on from incident light. Therefore, it is possible to obtain an optical multilayer film that is less expensive and more accurate than the optical multilayer film disclosed in PTL 1 cited above.

Note that the image pickup device 10 according to the embodiment includes the bandpass filter 115 described below in order to extract fluorescence that is focused on from light in the long-wavelength band containing fluorescence, the light having been separated by the dichroic film 103. When the bandpass filter 115 is used, light other than fluorescence is removed from light to be imaged on the fluorescence image pickup element 117, and a contrast of a fluorescence image is therefore improved.

A structure of the color separation prism 101 having the dichroic film 103 is not limited, and, in particular, the structure may have an arbitrary shape in the case where a size of the whole image pickup device 10 is not limited. However, in the case where the image pickup device 10 according to the embodiment is attached to various kinds of optical systems described above, such as a microscope and an endoscope, and functions as a camera head unit (CHU), the size of the image pickup device 10 is preferably reduced as much as possible. In order to reduce the size of the image pickup device 10, the color separation prism 101 preferably has a structure illustrated in FIG. 1A.

For example, the color separation prism 101 illustrated in FIG. 1A is a prism obtained by joining a first prism 105 and a second prism 107 to each other, and the first prism 105 and the second prism 107 are joined to each other via the dichroic film 103. That is, the dichroic film 103 is provided on an interface between the first prism 105 and the second prism 107.

Light belonging to the visible light wavelength band and light belonging to the fluorescence wavelength band (that is, incident light) are incident on the first prism 105, and the first prism 105 functions as a visible light optical path through which the light belonging to the visible light wavelength band is guided. The second prism 107 functions as a fluorescence optical path through which the light belonging to the fluorescence wavelength band is guided.

The incident light incident on the first prism 105 moves straight in the first prism 105 and is split by the dichroic film 103 that is obliquely provided on the optical axis into the light belonging to the visible light wavelength band and the light belonging to the fluorescence wavelength band.

The light belonging to the visible light wavelength band is reflected by the dichroic film 103 to be guided in the first prism 105. Herein, the reflected and split light belonging to the visible light wavelength band (that is, visible light rays) is totally reflected at a position A illustrated in FIG. 1A only once and is transmitted to the outside of the first prism 105. With this, an angle formed by a film deposition surface of the dichroic film 103 and the optical axis can be close to a right angle. Conversely, an installation angle of the dichroic film 103 according to the embodiment on the optical axis is set to satisfy a total reflection condition of visible light rays at the position A. Because the dichroic film 103 is disposed as described above, it is possible to suppress a change in spectral characteristic of the dichroic film 103 caused by a difference in angle of incidence between upper beams of light and lower beams of light even in the case where beams of light having a bright f-number are incident on the first prism 105. Therefore, it is possible to split wavelengths with high accuracy.

The visible light rays transmitted through the first prism 105 are guided to the visible light image pickup element 111. At this time, an infrared cut-off filter 113 may be provided between an emission surface of the first prism 105 and the visible light image pickup element 111. When the infrared cut-off filter 113 is provided, it is possible to remove infrared light contained in the visible light rays transmitted through the first prism 105, and therefore color reproducibility of a visible light image can be further improved. As the infrared cut-off filter 113, for example, a publicly-known absorption filter such as C5000 manufactured by HOYA CORPORATION can be used.

Meanwhile, the light belonging to the fluorescence wavelength band transmitted through the dichroic film 103 is incident on the second prism 107 and moves straight in the second prism 107. An end surface of the second prism 107, which is opposite to an end surface on which the dichroic film 103 is provided (in other words, an emission surface of the second prism 107 on a downstream side of the optical axis), is provided to be vertical to the optical axis, and the light belonging to the fluorescence wavelength band is transmitted to the outside of the second prism 107 while being vertical to the emission surface of the second prism 107.

The light belonging to the fluorescence wavelength band, which has been transmitted through the second prism 107, is incident on the bandpass filter 115 provided at a latter stage.

Heretofore, the color separation prism 101 according to the embodiment has been described in detail. Note that a material of the color separation prism 101 according to the embodiment is not particularly limited, and publicly-known optical glass or optical crystal can be used as appropriate in accordance with a wavelength of light to be guided in the color separation prism 101.

The color separation prism 101 according to the embodiment can be manufactured by cutting shapes of the first prism 105 and the second prism 107 from publicly-known optical glass or optical crystal and forming the dichroic film 103 between joining surfaces of the first prism 105 and the second prism 107 by a publicly-known method such as a vacuum deposition method. At this time, needless to say, the dichroic film 103 may be formed on the first prism 105 side, or the dichroic film 103 may be formed on the second prism 107.

The visible light image pickup element 111 will be described.

The visible light image pickup element 111 is provided at a latter stage of the color separation prism 101 (more specifically, at a latter stage of the first prism 105) and is an image pickup element on which light belonging to the visible light wavelength band separated by the dichroic film 103 is imaged. When the light belonging to the visible light wavelength band is imaged on the visible light image pickup element 111, a visible light image is generated. Herein, in the case where a fluorescence image described below and the visible light image are superimposed, it is preferable that, in order to position both the images more easily, the visible light image pickup element 111 be disposed so that an optical axis of visible light rays emitted from the first prism 105 is imaged on the center of the visible light image pickup element 111.

The visible light image pickup element 111 is preferably a single-plate image pickup element having an RGB color filter such as a CCD or a CMOS.

Note that, in the case where a 3-color separation prism is disposed at a latter stage of the first prism 105 to split the visible light rays emitted from the first prism 105 into three colors of an R component, a G component, and a B component, the visible light image pickup element 111 can be formed to have a three-plate configuration. With this configuration, it is possible to further improve the color reproducibility of a visible light image and therefore to implement image capturing processing with higher sen-sitivity.

The bandpass filter 115 will be described.

The bandpass filter 115 according to the embodiment is disposed between the color separation prism 101 (more specifically, the second prism 107) and the fluorescence image pickup element 117 and has a plane of incidence vertical to the optical axis. The bandpass filter 115 can extract only fluorescence that is focused on from light belonging to the fluorescence wavelength band separated by the dichroic film 103.

The bandpass filter 115 according to the embodiment has a bandpass characteristic that reflects light other than light in the fluorescence wavelength band and allows only the light in the fluorescence wavelength band to transmit therethrough. FIG. 3 shows an example of a spectral transmittance characteristic of the bandpass filter 115 according to the embodiment. In FIG. 3, a horizontal axis indicates a wavelength (unit: nm) of light incident on the bandpass filter 115, whereas a vertical axis indicates spectral transmittance (unit: %).

In the case where fluorescence having a wavelength of 832 nm belonging to the near-infrared band, the fluorescence being emitted from indocyanine green, is focused on, as shown in FIG. 3, the spectral transmittance of the bandpass filter 115 is preferably 90% or more in a wavelength band from 820 nm to 850 nm and is preferably 10% or less in a wavelength band from 400 nm to 805 nm and in a wavelength band from 860 nm to 1000 nm.

The transmittance of less than 90% in the wavelength band from 820 nm to 850 nm is not preferable because a ratio of fluorescence transmitted through the bandpass filter 115 is reduced and brightness of a fluorescence image is reduced. The transmittance exceeding 10% in the wavelength band from 400 nm to 805 nm and in the wavelength band from 860 nm to 1000 nm is not preferable because light from the outside other than fluorescence, such as excitation light having a wavelength of about 800 nm, is imaged on the fluorescence image pickup element 117 to thereby remarkably reduce a contrast of the fluorescence image.

In the case where a wavelength band of light transmitted through the bandpass filter 115 is extremely wider than the wavelength band from 820 nm to 850 nm, a near-infrared wavelength band contributing to formation of the fluorescence image is extremely wide. As a result, even in the case where the center of axial chromatic aberration can be corrected by the isolation distance $\Delta$ described below, a component having a longer wavelength forms a blur image and a contrast is reduced. This is not preferable.

In the case where a wavelength band of light transmitted through the bandpass filter 115 is extremely narrower than the wavelength band from 820 nm to 850 nm, the light transmitted through the bandpass filter 115 is close to one color and an effect of correcting axial chromatic aberration by using the isolation distance $\Delta$ described below is improved, but brightness of the fluorescence image is reduced. This is not preferable.

The bandpass filter 115 according to the embodiment can be manufactured by using a publicly-known optical material in accordance with a wavelength of fluorescence to be focused on. For example, the bandpass filter 115 according to the embodiment may be manufactured by depositing an optical multilayer film on a glass substrate corre-sponding to BK7 or may be manufactured by using visible absorption glass as a substrate, such as R80 manufactured by HOYA CORPORATION, and depositing an optical multilayer film on the substrate. With this, it is possible to suppress transmittance in a visible light region in a configuration including a glass substrate and to contribute to improvement in contrast of the fluorescence image.

Note that, although the bandpass filter 115 according to the embodiment can be deposited by a vacuum deposition method in the same way as the dichroic film 103, a spectral characteristic thereof is a narrow band and has a steep rise/fall shape, and therefore the number of layers of the film is greater than the number of layers of the dichroic film 103, i.e., is about several hundreds of layers. Thus, a deposition method that can secure high reliability, such as an ion beam sputtering method, is preferably employed instead of the vacuum deposition method.

Because the bandpass filter 115 according to the embodiment is disposed between the color separation prism 101 and the fluorescence image pickup element 117 and has a plane of incidence vertical to the optical axis, it is possible to suppress a change in spectral characteristic caused by a difference in angle of incidence between upper beams of light and lower beams of light even in the case where beams of light having a bright f-number are incident.

It is also considered that, in the case where the bandpass filter 115 is manufactured, the substrate is warped at the time of deposition. When such a warped component is incorporated into an image pickup system, resolution is reduced. Therefore, it is preferable to deposit bandpass films on both surfaces of the substrate because warpage on both the surfaces can be offset.

Although the emission surface of the second prism 107 and the bandpass filter 115 are isolated in FIG. 1A, the bandpass filter 115 may be joined to the emission surface of the second prism 107. This configuration is more preferable because a contact surface with air is reduced and therefore a risk of ghost flare can be reduced. Instead of separately forming the second prism 107 and the bandpass filter 115, a bandpass film may be deposited on the emission surface of the second prism 107. With this configuration, it is possible not only to reduce the above risk of ghost flare but also to remove a filter substrate. Therefore, further reduction in size and weight can be achieved.

The fluorescence image pickup element 117 will be described.

The fluorescence image pickup element 117 is provided at a latter stage of the bandpass filter 115 and is an image pickup element on which fluorescence extracted by the bandpass filter 115 is imaged. When the fluorescence extracted by the bandpass filter 115 is imaged on the fluorescence image pickup element 117, a fluorescence image is generated.

Herein, it is preferable to determine a fixed position of the fluorescence image pickup element 117 while shifting and adjusting the image pickup element 117 in a direction vertical to the optical axis so as to minimize an image shift of a fluorescence image from a visible light image generated by the visible light image pickup element 111. With this, in the case where a fluorescence image and a visible light image are superimposed, both the images can be positioned more easily. Note that, instead of the above adjustment of the position, the following method may be used: a fixed position of the fluorescence image pickup element 117 is determined and then a magnitude of an image shift of a fluorescence image from a visible light image, which is caused by tolerance of components, is specified; and a reading start position of a fluorescence image signal is shifted so as to minimize the magnitude of the specified image shift. When the method of adjusting the reading start position is used, the above adjustment processing can be omitted. This is advantageous in terms of costs.

The fluorescence image pickup element 117 may be a single-plate image pickup element having an RGB color filter such as a CCD or a CMOS.

The isolation distance $\Delta$ between the bandpass filter 115 and the fluorescence image pickup element 117 in the image pickup device 10 according to the embodiment will be described.

In the case where the image pickup device 10 according to the embodiment is actually used, a publicly-known imaging lens is attached at a former stage of the image pickup device 10 (more specifically, at a former stage of the color separation prism 101), and visible light rays and fluorescence are imaged on the respective image pickup elements. At this time, an imaging position of visible light rays and an imaging position of fluorescence are different due to axial chromatic aberration of the imaging lens, and, in the image pickup device 10 according to the embodiment, a shift between the imaging positions caused by this axial chromatic aberration is completely corrected by setting the isolation distance $\Delta$ illustrated in FIG. 1A.

That is, in the image pickup device 10 according to the embodiment, the fluorescence image pickup element 117 and the visible light image pickup element 111 are arranged so that an optical path difference $\Delta d$ between an optical path length of the fluorescence optical path imaged on the fluorescence image pickup element 117 via the color separation prism 101 and an optical path length of the visible light optical path imaged on the visible light image pickup element 111 via the color separation prism 101 corresponds to an amount of a shift between a fluorescence imaging position and a visible light imaging position (that is, a magnitude of the axial chromatic aberration), the shift being generated by the imaging lens attached at the former stage of the color separation prism 101. Specifically, the position of the fluorescence image pickup element 117 is controlled so that the isolation distance $\Delta$ illustrated in FIG. 1A is changed to be the optical path difference $\Delta d$.

Herein, the magnitude of the axial chromatic aberration caused by the imaging lens is changed in accordance with a configuration of an optical system of the imaging lens or the like and is different for each imaging lens. Therefore, in the case where the imaging lens attached at the former stage of the color separation prism 101 is not uniquely determined, it is important to control the isolation distance $\Delta$ in accordance with the imaging lens. In view of this, in such a case, the isolation distance $\Delta$ is set to be changeable and a fluorescence image focusing mechanism 119 is provided in the image pickup device 10 as schematically illustrated in FIG. 1A to control a length of the isolation distance $\Delta$.

As the fluorescence image focusing mechanism 119, for example, an actuator such as a stepping motor or a piezoelectric element can be used, or a cam mechanism or the like can also be used.

When any one of an optical unit 11 including the color separation prism 101, the visible light image pickup element 111, and the bandpass filter 115 and the fluorescence image pickup element 117 is moved along the optical axis by the fluorescence image focusing mechanism 119, the length of the isolation distance $\Delta$ can be controlled. At this time, the fluorescence image focusing mechanism 119 may move the position of the fluorescence image pickup element 117 along the optical axis after a position of the whole optical unit 11 is fixed, or the fluorescence image focusing mechanism 119 may move the position of the whole optical unit 11 along the optical axis after the position of the fluorescence image pickup element 117 is fixed.

A focusing method using the fluorescence image focusing mechanism 119 will be briefly described.

Publicly-known imaging lenses that are sold by various companies and are attachable to the image pickup device 10 according to the embodiment have a focusing mechanism. When the focusing mechanism is used, a visible light image can be focused (that is, visible light rays can be focused on the visible light image pickup element 111). At this time, in the imaging lens, axial chromatic aberration is generally corrected only in the visible light wavelength band, and therefore axial chromatic aberration in the near-infrared fluorescence wavelength band is not corrected in many cases. In the case where only the visible light image is focused, a fluorescence image is blurred. In view of this, the fluorescence image focusing mechanism 119 described above adjusts relative positions of the optical unit 11 and the fluorescence image pickup element 117, thereby focusing the fluorescence image. With this, it is possible to focus the fluorescence image while the visible light image is in a focused state.

In the case where the kind of the imaging lens to be used by a user is uniquely determined, the following method may be used, instead of providing the fluorescence image focusing mechanism 119 in the image pickup device 10. That is, as illustrated in FIG. 1B, after the magnitude Δd of the axial chromatic aberration of the imaging lens between visible light rays and fluorescence is measured, a fixation adhesion position of the fluorescence image pickup element 117 may be offset by Δd.

Note that a configuration and a method for changing the above isolation distance Δ are not particularly limited.

Heretofore, the image pickup device 10 according to the embodiment has been described in detail with reference to FIG. 1A to FIG. 3.

Note that, in the image pickup device 10 according to the embodiment, it is also possible to achieve an optical configuration in which the positions of the visible light image pickup element 111 and the fluorescence image pickup element 117 are switched. In this case, it is necessary to form the dichroic film 103 so that light in the visible light wavelength band is allowed to transmit therethrough and light in the fluorescence wavelength band is reflected. It is also necessary to dispose the bandpass filter 115 at a latter stage of the first prism 105.

A light source for observing a measurement target object (for example, an affected part on which a fluorescent probe is accumulated) with visible light is not particularly limited, and it is possible to use a xenon lamp which is a general white light source. In this case, a radiation spectrum includes both an excitation wavelength of the fluorescent probe and the visible light wavelength band, and therefore it is only necessary to prepare a single light source, which is advantageous. However, the radiation spectrum of the xenon lamp also includes the fluorescence wavelength band, and therefore a component in the fluorescence wavelength band of the xenon lamp is imaged on the fluorescence image pickup element 117, thereby reducing a fluorescence contrast. Thus, in the case where the xenon lamp is used, in order to prevent such reduction in contrast, a filter having a spectral transmittance characteristic that blocks the fluorescence band is preferably disposed in a light source.

<2-Piece Camera System Including Image Pickup Device>

An example of a 2-piece camera system including the image pickup device 10 according to the embodiment will be described with reference to FIG. 4. FIG. 4 is an explanatory diagram schematically illustrating an example of a configuration of a 2-piece camera system including the image pickup device according to the embodiment.

The 2-piece camera system described above can be achieved by using the image pickup device 10 according to the embodiment described above. As illustrated in FIG. 4, the 2-piece camera system includes the image pickup device 10 according to the embodiment and a camera control unit (CCU) 30.

Herein, a publicly-known imaging lens 20 is attached to the image pickup device 10, and both a visible light image and a fluorescence image are in a focused state by a focusing function of the imaging lens 20 and control of the isolation distance Δ in the image pickup device 10 according to the embodiment.

The image pickup device 10 independently generates a visible light image and a fluorescence image under image capturing control of the camera control unit 30 described below and outputs data of the generated captured images to the camera control unit 30.

The camera control unit 30 controls image capturing processing of the image pickup device 10 and superimposes the visible light image and the fluorescence image generated by the image pickup device 10 to generate a superimposed image. The camera control unit 30 can be achieved by any of various kinds of computers including a central processing unit (CPU), a read only memory (ROM), a random access memory (RAM), and the like. Note that an example of a detailed configuration of the camera control unit 30 will be described below.

The superimposed image generated by the camera control unit 30 is displayed as necessary on a display device 40 such as a display provided in the camera control unit 30 or the display device 40 such as a display provided outside the camera control unit 30. With this, a user of the 2-piece camera system can instantly grasp the superimposed image in which the visible light image and the fluorescence image are superimposed with satisfactory resolution.

Heretofore, an example of the configuration of the 2-piece camera system including the image pickup device 10 according to the embodiment has been briefly described with reference to FIG. 4.

<Configuration of Camera Control Unit that can be Used for Image Pickup Device>

An example of a configuration of the camera control unit 30 that can be used for the image pickup device 10 according to the embodiment will be briefly described with reference to FIG. 5. FIG. 5 is a block diagram showing an example of a configuration of a camera control unit that can be used for the image pickup device according to the embodiment.

As schematically illustrated in FIG. 5, the camera control unit 30 that can be used for the image pickup device 10 according to the embodiment mainly includes an image pickup device control unit 301, an image data acquisition unit 303, a superimposed image generation unit 305, a superimposed image output unit 307, a display control unit 309, and a storage unit 311.

The image pickup device control unit 301 is realized by, for example, a CPU, a ROM, a RAM, and a communication device. The image pickup device control unit 301 comprehensively controls the whole image capturing processing implemented in the image pickup device 10 according to the embodiment. In the case where the fluorescence image focusing mechanism 119 is provided in the image pickup device 10 according to the embodiment, the image pickup device control unit 301 also controls the fluorescence image focusing mechanism 119.

The image pickup device 10 according to the embodiment generates a visible light image and a fluorescence image at predetermined time intervals under the control of the image pickup device control unit 301 and outputs the generated images to the camera control unit 30 as necessary.

The image data acquisition unit 303 is realized by, for example, a CPU, a ROM, a RAM, and a communication device. The image data acquisition unit 303 acquires data of the visible light image and data of the fluorescence image output from the image pickup device 10 as necessary and outputs the data to the superimposed image generation unit 305 described below. The image data acquisition unit 303 may associate the acquired image data with a timestamp of date and time at which the image data has been acquired and store the image data associated with the timestamp as history information in the storage unit 311 described below.

The superimposed image generation unit 305 is realized by, for example, a CPU, a ROM, and a RAM. By using the visible light image and the fluorescence image output from the image data acquisition unit 303, the superimposed image generation unit 305 implements superimposing processing of the visible light image and the fluorescence image while positioning the visible light image and the fluorescence image, thereby generating a superimposed image in which those images are superimposed on each other. Note that processing for generating a superimposed image, which is implemented by the superimposed image generation unit 305, is not particularly limited, and a publicly-known image processing technology is applicable. The superimposed image generation unit 305 outputs data of the generated superimposed image to the superimposed image output unit 307 described below. The superimposed image generation unit 305 may associate the data of the generated superimposed image with a timestamp of date and time at which the image data has been generated and store the data associated with the timestamp as history information in the storage unit 311 described below.

The superimposed image output unit 307 is realized by, for example, a CPU, a ROM, a RAM, an output device, and a communication device. The superimposed image output unit 307 outputs the superimposed image generated by the superimposed image generation unit 305. More specifically, the superimposed image output unit 307 may output the data of the generated superimposed image to various kinds of image servers or the like provided outside the camera control unit 30 or may record the data in a publicly-known recording medium. The superimposed image output unit 307 may display the generated superimposed image on various kinds of display devices via the display control unit 309 described below in real time.

The display control unit 309 is realized by, for example, a CPU, a ROM, a RAM, an output device, and a communication device. The display control unit 309 performs display control when the superimposed image generated by the superimposed image generation unit 305 is displayed on an output device such as the display included in the camera control unit 30, an output device provided outside the camera control unit 30, or the like. With this, a user of the image pickup device 10 can instantly see a desired superimposed image.

The storage unit 311 is realized by, for example, a RAM, a storage device, or the like included in the camera control unit 30 according to the embodiment. In the storage unit 311, for example, various kinds of data to be used by the camera control unit 30 according to the embodiment to control the image pickup device 10 are recorded. The storage unit 311 records, as appropriate, various parameters to be stored when the camera control unit 30 according to the embodiment performs some processing and progress of the processing, various kinds of databases and programs, or the like.

The image pickup device control unit 301, the image data acquisition unit 303, the superimposed image generation unit 305, the superimposed image output unit 307, the display control unit 309, and the like can freely perform read/write processing of data in the storage unit 311 that stores such various kinds of information.

Heretofore, an example of the function of the camera control unit 30 according to the embodiment has been described. Each of the structural elements described above may be configured using a general-purpose material or circuit or may be configured by hardware dedicated to the function of each structural element. Further, all the functions of the structural elements may be performed by a CPU or the like. Accordingly, the configuration to be used can be changed as appropriate in accordance with the technical level at the time of carrying out the present embodiment.

Note that a computer program for realizing each function of the above camera control unit 30 according to the embodiment can be prepared and mounted on a personal computer or the like. It is also possible to provide a computer readable recording medium in which such a computer program is stored. The recording medium is, for example, a magnetic disk, an optical disk, a magneto-optical disk, or a flash memory. For example, the above computer program may also be distributed via a network, instead of using the recording medium.

<Microscope Image Pickup System Including Image Pickup Device>

A microscope image pickup system 1000 including the image pickup device 10 according to the embodiment will be briefly described with reference to FIG. 6. FIG. 6 is an explanatory diagram schematically illustrating an example of a configuration of a microscope image pickup system including the image pickup device according to the embodiment.

The microscope image pickup system can be constructed by combining the image pickup device 10 described above (more specifically, the 2-piece camera system including the image pickup device 10) and a microscope optical system.

As schematically illustrated in FIG. 6, the microscope image pickup system 1000 includes the image pickup device 10, the CCU 30, the display device 40, and a microscope optical system 50.

Herein, the image pickup device 10, the CCU 30, and the display device 40 have configurations similar to the configurations thereof included in the 2-piece camera system described above and therefore have similar effects. Thus, hereinafter, detailed description thereof will be omitted.

As schematically illustrated in FIG. 6, the microscope optical system 50 includes a light source 501, a stage 503, an objective lens 505, a revolver 507, and a lens barrel 509, and the lens barrel 509 mainly includes an eyepiece lens 511, an imaging lens 513, and a beam splitter BS.

Illumination light emitted from the light source 501 is reflected by a mirror M or the like as appropriate to be guided to a sample S placed on the stage 503. The objective lens 505 forms a magnified image of this sample. The beam splitter BS provided in the lens barrel reflects a part of the image of the sample imaged by the objective lens 505 and guides the part to the eyepiece lens 511. The guided image of the sample is emitted to be substantially afocal by the eyepiece lens 511. With this, an observer of the microscope optical system 50 can observe the magnified image of the sample with the naked eye.

Meanwhile, the imaging lens 513 provided in the lens barrel 509 images the image of the sample transmitted through the beam splitter BS on the visible light image pickup element 111 and the fluorescence image pickup element 117 of the image pickup device 10.

The revolver 507 has a function of holding the objective lens 505 on an observation optical axis of the microscope, and the lens can be switched to another objective lens 505 attached to the revolver 507 by operating a rotating mechanism of the revolver 507.

A generation amount A of axial chromatic aberration between visible light and fluorescence is changed when the objective lens 505 is changed as described above.

Hereinafter, a focusing method using the fluorescence image focusing mechanism 119 will be briefly described. A visible light image can be focused by moving the stage 503 or the objective lens 505 upward and downward in an optical axis direction to change a working distance. At this time, in the objective lens 505, axial chromatic aberration is generally corrected only in the visible light wavelength band, and therefore axial chromatic aberration in the near-infrared fluorescence wavelength band is not corrected in many cases. In the case where only the visible light image is focused, a fluorescence image is blurred. Therefore, the fluorescence image is focused by the fluorescence image focusing mechanism 119 described above. With this, it is possible to focus the fluorescence image while the visible light image is in a focused state.

Those captured images generated as described above are output to the CCU 30, and the CCU 30 superimposes the images to thereby generate a superimposed image. The generated superimposed image is displayed on the display device 40 under the control of the CCU 30.

Heretofore, the microscope image pickup system 1000 including the image pickup device 10 according to the embodiment has been briefly described with reference to FIG. 6.

<Another Example of Configuration of Image Pickup Device>

The image pickup device 10 according to the embodiment described above is attachable to, for example, various kinds of medical endoscopes such as a rigid endoscope and various kinds of industrial endoscopes. Hereinafter, a medical endoscope will be exemplified and a configuration of the image pickup device 10 attachable to the medical endoscope will be briefly described with reference to FIG. 7A and FIG. 7B. FIG. 7A and FIG. 7B are explanatory diagrams each of which schematically illustrates another example of the configuration of the image pickup device according to the embodiment.

In the case where the image pickup device 10 according to the embodiment is connected to various kinds of endoscopes such as a rigid endoscope, as illustrated in FIG. 7A and FIG. 7B, a coupler optical system 25 in which axial chromatic aberration has been corrected at least in the visible light wavelength band is attached as an imaging lens at a former stage of the image pickup device 10. With this, an aerial image of a measurement target object (for example, an affected part on which a fluorescent probe is accumulated) generated by the endoscope can be connected to the image pickup device 10.

As illustrated in FIG. 7A and FIG. 7B, a visible light image focusing mechanism 121 is provided for the coupler optical system 25 in the image pickup device 10 to be attached to the endoscope. The visible light image focusing mechanism 121 is a mechanism for moving only the coupler optical system 25 in the optical axis direction to focus a visible light image on the visible light image pickup element 111.

As the visible light image focusing mechanism 121, for example, an actuator such as a stepping motor or a piezoelectric element can be used, or a cam mechanism or the like can be used.

Note that, in FIG. 7A and FIG. 7B, the configurations of the image pickup device 10 excluding the visible light image focusing mechanism 121 are similar to the cases illustrated in FIG. 1A and FIG. 1B, except that the optical unit 11 in FIG. 7A further includes the coupler optical system 25. Therefore, hereinafter, detailed description thereof will be omitted.

<Endoscope Image Pickup System Including Image Pickup Device>

An endoscope image pickup system 2000 including the image pickup device 10 illustrated in FIG. 7A and FIG. 7B will be briefly described with reference to FIG. 8. FIG. 8 is an explanatory diagram schematically illustrating an example of a configuration of an endoscope image pickup system including the image pickup device according to the embodiment.

The endoscope image pickup system can be constructed by combining the image pickup device 10 described above (more specifically, the 2-piece camera system including the image pickup device 10) and an endoscope optical system.

As schematically illustrated in FIG. 8, the endoscope image pickup system 2000 includes the image pickup device 10 illustrated in FIG. 7A or FIG. 7B, the CCU 30, the display device 40, and an endoscope optical system 60.

Herein, the image pickup device 10, the CCU 30, and the display device 40 have configurations similar to the configurations thereof described above and therefore have similar effects. Thus, hereinafter, detailed description thereof will be omitted.

The endoscope (rigid endoscope) optical system 60 includes an objective lens 601, a plurality of relay lenses 603, and an eyepiece lens 605 in order from an object side (subject side). The objective lens 601 forms an aerial image of a subject, and the relay lenses 603 performs unmagnified relay imaging of the formed aerial image multiple times. Thereafter, the eyepiece lens 605 performs afocal imaging of the last aerial image, and thus the aerial image can be observed with the naked eye.

Herein, the endoscope (rigid endoscope) is mainly for observing an aerial image with the naked eye, and therefore, in order to image the aerial image generated by the endoscope optical system 60 on the image pickup element of the image pickup device 10, the coupler optical system 25 serving as the imaging lens is disposed between the eyepiece lens 605 and the image pickup device 10.

A focusing method using the fluorescence image focusing mechanism 119 and the visible light image focusing mechanism 121 will be briefly described.

In the endoscope image pickup system 2000 according to the embodiment, first, the visible light image focusing mechanism 121 moves only the coupler optical system 25 in the optical axis direction to thereby focus a visible light image. In the coupler optical system 25, axial chromatic aberration is corrected only in the visible light wavelength band as described above, and therefore a fluorescence image is not appropriately focused and is blurred. After the visible light image focusing mechanism 121 focuses the visible light image, the fluorescence image focusing mechanism 119 changes the isolation distance Δ between the optical unit 11 to which the coupler optical system 25 is integrally attached and the fluorescence image pickup element 117, thereby focusing the fluorescence image. With this, it is possible to focus the fluorescence image while the visible light image is in a focused state.

Those captured images generated as described above are output to the CCU 30, and the CCU 30 superimposes the images to thereby generate a superimposed image. The generated superimposed image is displayed on the display device 40 under the control of the CCU 30.

Heretofore, the endoscope image pickup system 2000 including the image pickup device 10 according to the embodiment has been briefly described with reference to FIG. 8.

(Hardware Configuration)

Next, the hardware configuration of the camera control unit (CCU) 30 according to the embodiment of the present disclosure will be described in detail with reference to FIG. 9. FIG. 9 is a block diagram for illustrating the hardware configuration of the CCU 30 according to the embodiment of the present disclosure.

The CCU 30 mainly includes a CPU 901, a ROM 903, and a RAM 905. Furthermore, the CCU 30 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing apparatus and a control device, and controls the overall operation or a part of the operation of the CCU 30 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The input device 915 is an operation mechanism operated by a user, such as a mouse, a keyboard, a touch panel, buttons, a switch and a lever. Also, the input device 915 may be a remote control mechanism (a so-called remote control) using, for example, infrared light or other radio waves, or may be an externally connected apparatus 929 such as a mobile phone or a PDA conforming to the operation of the CCU 30. Furthermore, the input device 915 generates an input signal based on, for example, information which is input by a user with the above operation mechanism, and is configured from an input control circuit for outputting the input signal to the CPU 901. The user of the CCU 30 can input various data to the CCU 30 and can instruct the information processing apparatus 10 to perform processing by operating this input apparatus 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processings performed by the CCU 30. More specifically, the display device displays, in the form of texts or images, a result obtained by various processes performed by the CCU 30. On the other hand, the audio output device converts an audio signal such as reproduced audio data and sound data into an analog signal, and outputs the analog signal.

The storage device 919 is a device for storing data configured as an example of a storage unit of the CCU 30. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the CCU 30 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the CCU 30. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the CCU 30 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the CCU 30 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

It should be understood by those skilled in the art that various modifications, combinations, sub-combinations and alterations may occur depending on design re-quirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A medical imaging device including:

a color separation prism that has a dichroic film configured to split light into first light belonging to a visible light wavelength band and second light belonging to a fluorescence wavelength band;

a fluorescence image sensor that is provided at an output side of the color separation prism and that is configured to image at least part of the second light belonging to the fluorescence wavelength band separated by the dichroic film;

a visible light image sensor that is provided at the output side of the color separation prism and that is configured to image at least part of the first light belonging to the visible light wavelength band separated by the dichroic film; and a bandpass filter that is disposed between the color separation prism and the fluorescence image sensor, wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and wherein the fluorescence imaging position is an imaging position of filtered second light, which results from passing the second light through the bandpass filter, such that the amount of shift is based on the filtered second light.

(2)

The medical imaging device according to (1), wherein each of the fluorescence image sensor and the visible light image sensor is fixed such that the optical path difference corresponds to the amount of the shift.

(3)

The medical imaging device according to (1), wherein the fluorescence image sensor is provided such that an isolation distance from the bandpass filter is changeable, further including:

a fluorescence image focusing actuator configured to focus the second light belonging to the fluorescence wavelength band separated by the dichroic film on the fluorescence image sensor, and wherein the fluorescence image focusing actuator controls the isolation distance in accordance with the imaging lens attached at the input side of the color separation prism such that the optical path difference corresponds to the amount of the shift.

(4)

The medical imaging device according to (3), wherein a coupler optical lens assembly, in which axial chromatic aberration has been corrected at least in the visible light wavelength band, is provided as the imaging lens at the input side of the color separation prism, wherein the fluorescence image sensor is provided such that the isolation distance from the bandpass filter is changeable, wherein the image sensor further includes a visible light image focusing actuator configured to focus the first light belonging to the visible light wavelength band separated by the dichroic film on the visible light image sensor, wherein the visible light image focusing actuator moves the coupler optical lens assembly in an optical axis direction to focus the first light belonging to the visible light wavelength band separated by the dichroic film on the visible light image sensor, and wherein the fluorescence image focusing actuator controls the isolation distance such that the optical path difference, obtained when the first light belonging to the visible light wavelength band is focused on the visible light image sensor, corresponds to the amount of the shift.

(5)

The medical imaging device according to (3)-(4), wherein the fluorescence image focusing actuator controls the isolation distance by moving the bandpass filter in an optical axis direction with respect to the fluorescence image sensor.

(6)

The medical imaging device according to (3)-(5), wherein the fluorescence image focusing actuator controls the isolation distance by moving the fluorescence image sensor in an optical axis direction with respect to the bandpass filter.

(7)

The medical imaging device according to (1)-(6), wherein the dichroic film splits incident light into the second light belonging to a predetermined fluorescence wavelength band, light of a band of longer wavelengths than the predetermined fluorescence wavelength band, and light belonging to a band of shorter wavelengths than the predetermined fluorescence wavelength band.

(8)

The medical imaging device according to (1)-(7), wherein the color separation prism is a prism comprising a first prism on which the first light belonging to the visible light wavelength band and the second light belonging to the fluorescence wavelength band are incident, the first prism functioning as the visible light optical path through which the first light belonging to the visible light wavelength band is guided, and a second prism functioning as the fluorescence optical path through which the second light belonging to the fluorescence wavelength band is guided, to each other, wherein the first prism and the second prism are joined to each other via the dichroic film, wherein the second light belonging to the fluorescence wavelength band separated by the dichroic film moves straight in the second prism to be vertically incident on the bandpass filter, and wherein the first light belonging to the visible light wavelength band separated by the dichroic film is totally reflected in the first prism and is then imaged on the visible light image sensor.

(9)

The medical imaging device according to (1)-(8), further including a 3-color separation prism configured to split the first light belonging to the visible light wavelength band emitted from the color separation prism into three colors of an R component, a G component, and a B component.

(10)

The medical imaging device according to (1)-(9), wherein the dichroic film has transmittance of 90% or more in a wavelength band from 780 nm to 880 nm and has transmittance of 10% or less in a wavelength band from 400 nm to 720 nm.

(11)

The medical imaging device according to (1)-(10), wherein the bandpass filter has transmittance of 90% or more in a wavelength band from 820 nm to 850 nm and has transmittance of 10% or less in a wavelength band from 400 nm to 805 nm and in a wavelength band from 860 nm to 1000 nm.

(12)

A medical microscopic system including:

a microscopic optical lens assembly including at least an objective lens and an imaging lens; and an imaging device configured to capture a magnified image of an object, wherein the imaging device includes a color separation prism that has a dichroic film configured to split light into first light belonging to the visible light wavelength band and second light belonging to the fluorescence wavelength band, a fluorescence image sensor that is provided at an output side of the color separation prism and that is configured to image at least part of the second light belonging to the fluorescence wavelength band separated by the dichroic film, a visible light image sensor that is provided at the output side of the color separation prism and that is configured to image at least part of the first light belonging to the visible light wavelength band separated by the dichroic film, and a bandpass filter that is disposed between the color separation prism and the fluorescence image sensor, wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and wherein the fluorescence imaging position is an imaging position of filtered second light, which results from passing the second light through the bandpass filter, such that the amount of shift is based on the filtered second light.

(13)

The medical microscope imaging system according to (12), wherein each of the fluorescence image sensor and the visible light image sensor is fixed such that the optical path difference corresponds to the amount of the shift.

(14)

The medical microscope imaging system according to (12), wherein the fluorescence image sensor is provided such that an isolation distance from the bandpass filter is changeable, wherein the imaging device further includes a fluorescence image focusing actuator configured to focus the second light belonging to the fluorescence wavelength band separated by the dichroic film on the fluorescence image sensor, and wherein the fluorescence image focusing actuator controls the isolation distance in accordance with the imaging lens attached at the input side of the color separation prism such that the optical path difference corresponds to the amount of the shift.

(15)

The medical microscope imaging system according to (14), wherein a coupler optical lens assembly, in which axial chromatic aberration has been corrected at least in the visible light wavelength band, is provided as the imaging lens at the input side of the color separation prism, wherein the fluorescence image sensor is provided such that the isolation distance from the bandpass filter is changeable, wherein the image sensor further includes a visible light image focusing actuator configured to focus the first light belonging to the visible light wavelength band separated by the dichroic film on the visible light image sensor, wherein the visible light image focusing actuator moves the coupler optical lens assembly in an optical axis direction to focus the first light belonging to the visible light wavelength band separated by the dichroic film on the visible light image sensor, and wherein the fluorescence image focusing actuator controls the isolation distance such that the optical path difference, obtained when the first light belonging to the visible light wavelength band is focused on the visible light image sensor, corresponds to the amount of the shift.

(16)

The medical microscope imaging system according to (14)-(15), wherein the fluorescence image focusing actuator controls the isolation distance by moving the bandpass filter in an optical axis direction with respect to the fluorescence image sensor or moving the fluorescence image sensor in an optical axis direction with respect to the bandpass filter.

(17)

The medical microscope imaging system according to (12)-(16), wherein the color separation prism is a prism comprising a first prism on which the first light belonging to the visible light wavelength band and the second light belonging to the fluorescence wavelength band are incident, the first prism functioning as the visible light optical path through which the first light belonging to the visible light wavelength band is guided, and a second prism functioning as the fluorescence optical path through which the second light belonging to the fluorescence wavelength band is guided, to each other, wherein the first prism and the second prism are joined to each other via the dichroic film, wherein the second light belonging to the fluorescence wavelength band separated by the dichroic film moves straight in the second prism to be vertically incident on the bandpass filter, and wherein the first light belonging to the visible light wavelength band separated by the dichroic film is totally reflected in the first prism and is then imaged on the visible light image sensor.

(18)

The medical microscope imaging system according to (12)-(17),
wherein the dichroic film has transmittance of 90% or more in a wavelength band from 780 nm to 880 nm and has transmittance of 10% or less in a wavelength band from 400 nm to 720 nm.

(19)

The medical microscope imaging system according to (12)-(18),
wherein the bandpass filter has transmittance of 90% or more in a wavelength band from 820 nm to 850 nm and has transmittance of 10% or less in a wavelength band from 400 nm to 805 nm and in a wavelength band from 860 nm to 1000 nm.

(20)

An endoscopic system including:
an endoscopic optical lens assembly;
an imaging device configured to capture an image of an object; and
an coupler optical lens assembly that is provided between the endoscopic optical lens assembly and the imaging device,
wherein the imaging device includes
a color separation prism that has a dichroic film configured to split light into first light belonging to the visible light wavelength band and second light belonging to the fluorescence wavelength band,
a fluorescence image sensor that is provided at an output side of the color separation prism and that is configured to image at least part of the second light belonging to the fluorescence wavelength band separated by the dichroic film,
a visible light image sensor that is provided at the output side of the color separation prism and that is configured to image at least part of the first light belonging to the visible light wavelength band separated by the dichroic film, and
a bandpass filter that is disposed between the color separation prism and the fluorescence image sensor, and
wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and
wherein the fluorescence imaging position is an imaging position of filtered second light, which results from passing the second light through the bandpass filter, such that the amount of shift is based on the filtered second light.

REFERENCE SIGNS LIST

10 image pickup device
20 imaging lens
30 camera control unit (CCU)
40 display device
50 microscope optical system
60 endoscope optical system
101 color separation prism
103 dichroic film
105 first prism
107 second prism
111 image pickup element for capturing visible light image
113 infrared cut-off filter
115 bandpass filter
117 fluorescence image pickup element
119 fluorescence image focusing mechanism
121 visible light image focusing mechanism
1000 microscope image pickup system
2000 endoscope image pickup system

The invention claimed is:

1. A medical imaging device comprising:
a color separation prism that has a dichroic film configured to split light into first light belonging to a visible light wavelength band and second light belonging to a fluorescence wavelength band;
a fluorescence image sensor that is provided at an output side of the color separation prism and that is configured to image at least part of the second light belonging to the fluorescence wavelength band separated by the dichroic film;
a visible light image sensor that is provided at the output side of the color separation prism and that is configured to image at least part of the first light belonging to the visible light wavelength band separated by the dichroic film; and
a bandpass filter that is disposed between the color separation prism and the fluorescence image sensor,
wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and
wherein the fluorescence imaging position is an imaging position of filtered second light, which results from passing the second light through the bandpass filter, such that the amount of shift is based on the filtered second light.

2. The medical imaging device according to claim 1,
wherein each of the fluorescence image sensor and the visible light image sensor is fixed such that the optical path difference corresponds to the amount of the shift.

3. The medical imaging device according to claim 1,
wherein the fluorescence image sensor is provided such that an isolation distance from the bandpass filter is changeable,
further comprising:
a fluorescence image focusing actuator configured to focus the second light belonging to the fluorescence wavelength band separated by the dichroic film on the fluorescence image sensor, and
wherein the fluorescence image focusing actuator controls the isolation distance in accordance with the imaging lens attached at the input side of the color separation prism such that the optical path difference corresponds to the amount of the shift.

4. The medical imaging device according to claim 3,
wherein a coupler optical lens assembly, in which axial chromatic aberration has been corrected at least in the visible light wavelength band, is provided as the imaging lens at the input side of the color separation prism, wherein the fluorescence image sensor is provided such that the isolation distance from the bandpass filter is changeable, wherein the image sensor further includes a visible light image focusing actuator configured to focus the first light belonging to the visible light wavelength band separated by the dichroic film on the visible light image sensor, wherein the visible light image focusing actuator moves the coupler optical lens assembly in an optical axis direction to focus the first light belonging to the visible light wavelength band separated by the dichroic film on the visible light image sensor, and wherein the fluorescence image focusing actuator controls the isolation distance such that the optical path difference, obtained when the first light belonging to the visible light wavelength band is focused on the visible light image sensor, corresponds to the amount of the shift.

5. The medical imaging device according to claim 3, wherein the fluorescence image focusing actuator controls the isolation distance by moving the bandpass filter in an optical axis direction with respect to the fluorescence image sensor.

6. The medical imaging device according to claim 3, wherein the fluorescence image focusing actuator controls the isolation distance by moving the fluorescence image sensor in an optical axis direction with respect to the bandpass filter.

7. The medical imaging device according to claim 1, wherein the dichroic film splits incident light into the second light belonging to a predetermined fluorescence wavelength band, light of a band of longer wavelengths than the predetermined fluorescence wavelength band, and light belonging to a band of shorter wavelengths than the predetermined fluorescence wavelength band.

8. The medical imaging device according to claim 1, wherein the color separation prism is a prism comprising a first prism on which the first light belonging to the visible light wavelength band and the second light belonging to the fluorescence wavelength band are incident, the first prism functioning as the visible light optical path through which the first light belonging to the visible light wavelength band is guided, and a second prism functioning as the fluorescence optical path through which the second light belonging to the fluorescence wavelength band is guided, to each other, wherein the first prism and the second prism are joined to each other via the dichroic film, wherein the second light belonging to the fluorescence wavelength band separated by the dichroic film moves straight in the second prism to be vertically incident on the bandpass filter, and wherein the first light belonging to the visible light wavelength band separated by the dichroic film is totally reflected in the first prism and is then imaged on the visible light image sensor.

9. The medical imaging device according to claim 1, further comprising a 3-color separation prism configured to split the first light belonging to the visible light wavelength band emitted from the color separation prism into three colors of an R component, a G component, and a B component.

10. The medical imaging device according to claim 1, wherein the dichroic film has transmittance of 90% or more in a wavelength band from 780 nm to 880 nm and has transmittance of 10% or less in a wavelength band from 400 nm to 720 nm.

11. The medical imaging device according to claim 1, wherein the bandpass filter has transmittance of 90% or more in a wavelength band from 820 nm to 850 nm and has transmittance of 10% or less in a wavelength band from 400 nm to 805 nm and in a wavelength band from 860 nm to 1000 nm.

12. A medical microscopic system comprising:
a microscopic optical lens assembly including at least an objective lens and an imaging lens; and
an imaging device configured to capture a magnified image of an object,
wherein the imaging device includes
a color separation prism that has a dichroic film configured to split light into first light belonging to the visible light wavelength band and second light belonging to the fluorescence wavelength band,
a fluorescence image sensor that is provided at an output side of the color separation prism and that is configured to image at least part of the second light belonging to the fluorescence wavelength band separated by the dichroic film,
a visible light image sensor that is provided at the output side of the color separation prism and that is configured to image at least part of the first light belonging to the visible light wavelength band separated by the dichroic film, and
a bandpass filter that is disposed between the color separation prism and the fluorescence image sensor,
wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and
wherein the fluorescence imaging position is an imaging position of filtered second light, which results from passing the second light through the bandpass filter, such that the amount of shift is based on the filtered second light.

13. The medical microscope imaging system according to claim 12,
wherein each of the fluorescence image sensor and the visible light image sensor is fixed such that the optical path difference corresponds to the amount of the shift.

14. The medical microscope imaging system according to claim 12,
wherein the fluorescence image sensor is provided such that an isolation distance from the bandpass filter is changeable,
wherein the imaging device further includes a fluorescence image focusing actuator configured to focus the second light belonging to the fluorescence wavelength band separated by the dichroic film on the fluorescence image sensor, and
wherein the fluorescence image focusing actuator controls the isolation distance in accordance with the imaging lens attached at the input side of the color separation prism such that the optical path difference corresponds to the amount of the shift.

15. The medical microscope imaging system according to claim 14,
wherein a coupler optical lens assembly, in which axial chromatic aberration has been corrected at least in the visible light wavelength band, is provided as the imaging lens at the input side of the color separation prism,
wherein the fluorescence image sensor is provided such that the isolation distance from the bandpass filter is changeable,
wherein the image sensor further includes a visible light image focusing actuator configured to focus the first light belonging to the visible light wavelength band separated by the dichroic film on the visible light image sensor,
wherein the visible light image focusing actuator moves the coupler optical lens assembly in an optical axis direction to focus the first light belonging to the visible light wavelength band separated by the dichroic film on the visible light image sensor, and
wherein the fluorescence image focusing actuator controls the isolation distance such that the optical path difference, obtained when the first light belonging to the visible light wavelength band is focused on the visible light image sensor, corresponds to the amount of the shift.

16. The medical microscope imaging system according to claim 14,
wherein the fluorescence image focusing actuator controls the isolation distance by moving the bandpass filter in an optical axis direction with respect to the fluorescence image sensor or moving the fluorescence image sensor in an optical axis direction with respect to the bandpass filter.

17. The medical microscope imaging system according to claim 12,
wherein the color separation prism is a prism comprising a first prism on which the first light belonging to the visible light wavelength band and the second light belonging to the fluorescence wavelength band are incident, the first prism functioning as the visible light optical path through which the first light belonging to the visible light wavelength band is guided, and
a second prism functioning as the fluorescence optical path through which the second light belonging to the fluorescence wavelength band is guided, to each other,
wherein the first prism and the second prism are joined to each other via the dichroic film,
wherein the second light belonging to the fluorescence wavelength band separated by the dichroic film moves straight in the second prism to be vertically incident on the bandpass filter, and
wherein the first light belonging to the visible light wavelength band separated by the dichroic film is totally reflected in the first prism and is then imaged on the visible light image sensor.

18. The medical microscope imaging system according to claim 12,
wherein the dichroic film has transmittance of 90% or more in a wavelength band from 780 nm to 880 nm and has transmittance of 10% or less in a wavelength band from 400 nm to 720 nm.

19. The medical microscope imaging system according to claim 12,
wherein the bandpass filter has transmittance of 90% or more in a wavelength band from 820 nm to 850 nm and has transmittance of 10% or less in a wavelength band from 400 nm to 805 nm and in a wavelength band from 860 nm to 1000 nm.

20. An endoscopic system comprising:
an endoscopic optical lens assembly;
an imaging device configured to capture an image of an object; and
an coupler optical lens assembly that is provided between the endoscopic optical lens assembly and the imaging device,
wherein the imaging device includes
a color separation prism that has a dichroic film configured to split light into first light belonging to the visible light wavelength band and second light belonging to the fluorescence wavelength band,
a fluorescence image sensor that is provided at an output side of the color separation prism and that is configured to image at least part of the second light belonging to the fluorescence wavelength band separated by the dichroic film,
a visible light image sensor that is provided at the output side of the color separation prism and that is configured to image at least part of the first light belonging to the visible light wavelength band separated by the dichroic film, and
a bandpass filter that is disposed between the color separation prism and the fluorescence image sensor, and
wherein the fluorescence image sensor and the visible light image sensor are arranged such that an optical path difference between an optical path length of a fluorescence optical path for the second light imaged on the fluorescence image sensor via the color separation prism and an optical path length of a visible light optical path for the first light imaged on the visible light image sensor via the color separation prism corresponds to an amount of a shift between a fluorescence imaging position and a visible light imaging position, the shift being generated by an imaging lens positioned at an input side of the color separation prism, and
wherein the fluorescence imaging position is an imaging position of filtered second light, which results from passing the second light through the bandpass filter, such that the amount of shift is based on the filtered second light.

* * * * *